(12) United States Patent
Kobayashi et al.

(10) Patent No.: US 10,694,982 B2
(45) Date of Patent: Jun. 30, 2020

(54) IMAGING APPARATUS, AUTHENTICATION PROCESSING APPARATUS, IMAGING METHOD, AUTHENTICATION PROCESSING METHOD

(71) Applicant: SONY CORPORATION, Tokyo (JP)

(72) Inventors: Naoko Kobayashi, Tokyo (JP);
Kenichiro Nakamura, Saitama (JP);
Yusuke Sato, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 49 days.

(21) Appl. No.: 16/095,683

(22) PCT Filed: Feb. 10, 2017

(86) PCT No.: PCT/JP2017/005015
§ 371 (c)(1),
(2) Date: Oct. 22, 2018

(87) PCT Pub. No.: WO2017/187718
PCT Pub. Date: Nov. 2, 2017

(65) Prior Publication Data
US 2019/0125221 A1    May 2, 2019

(30) Foreign Application Priority Data

Apr. 28, 2016  (JP) .................................. 2016-091816

(51) Int. Cl.
*A61B 5/1172*        (2016.01)
*G06K 9/00*          (2006.01)
(Continued)

(52) U.S. Cl.
CPC .......... *A61B 5/1172* (2013.01); *G02B 6/0023* (2013.01); *G06K 9/0004* (2013.01);
(Continued)

(58) Field of Classification Search
CPC ..... G06K 9/00013; G06K 2009/00932; G06K 2009/0006; G06K 9/00; G06K 9/00006;
(Continued)

(56) References Cited

U.S. PATENT DOCUMENTS

| 7,245,745 | B2 * | 7/2007 | Nagasaka | G06K 9/00 382/115 |
| 8,155,402 | B2 * | 4/2012 | Kiyomizu | G06K 9/00013 382/115 |

(Continued)

FOREIGN PATENT DOCUMENTS

| CN | 101201896 A | 6/2008 |
| CN | 101357065 A | 2/2009 |

(Continued)

OTHER PUBLICATIONS

International Search Report and Written Opinion of PCT Application No. PCT/JP2017/005015, dated Mar. 14, 2017, 10 pages of ISRWO.

*Primary Examiner* — Koosha Sharifi-Tafreshi
(74) *Attorney, Agent, or Firm* — Chip Law Group

(57) ABSTRACT

An imaging apparatus includes a first light guide plate having a mounting surface including a mounting region where a part of a living body is to be mounted, a second light guide plate provided on the mounting surface excluding the mounting region, at least one first light source provided on an edge portion of the first light guide plate and configured to radiate first irradiation light of a prescribed wavelength to an interior of the first light guide plate, at least one second light source provided on an edge portion of the second light guide plate and configured to radiate second irradiation light of a prescribed wavelength to an interior of the second light guide plate, and an imaging unit placed on a side of a surface of the first light guide plate on an opposite side to the second light guide plate.

20 Claims, 20 Drawing Sheets

(51) Int. Cl.
*F21V 8/00* (2006.01)
*G06T 1/00* (2006.01)

(52) U.S. Cl.
CPC ..... *G06K 9/00013* (2013.01); *G06K 9/00087* (2013.01); *G06K 9/00114* (2013.01); *G06T 1/0007* (2013.01); *G06K 2009/00932* (2013.01)

(58) Field of Classification Search
CPC ............ G06K 9/0004; G06K 9/00046; G06K 9/00073; A61B 5/1172
See application file for complete search history.

(56) References Cited

U.S. PATENT DOCUMENTS

| | | |
|---|---|---|
| 2003/0103686 A1* | 6/2003 | Ogura ................ G06K 9/00013 382/321 |
| 2008/0175444 A1 | 7/2008 | Maro et al. |
| 2009/0036783 A1 | 2/2009 | Kishima |
| 2011/0013074 A1 | 1/2011 | Ichimura et al. |
| 2014/0194748 A1 | 7/2014 | Yamamoto et al. |
| 2018/0018494 A1* | 1/2018 | Wu ..................... G06K 9/00046 |

FOREIGN PATENT DOCUMENTS

| | | |
|---|---|---|
| CN | 101953689 A | 1/2011 |
| EP | 2278529 A1 | 1/2011 |
| JP | 2003-331268 A | 11/2003 |
| JP | 2007-179434 A | 7/2007 |
| JP | 2008-113860 A | 5/2008 |
| JP | 2008-269259 A | 11/2008 |
| JP | 2008-297230 A | 12/2008 |
| JP | 2009-028427 A | 2/2009 |
| JP | 2011-022860 A | 2/2011 |
| JP | 2014-135535 A | 7/2014 |
| JP | 2015-127852 A | 7/2015 |
| KR | 2009-0013068 A | 2/2009 |
| TW | 201539330 A | 10/2015 |
| WO | 2015/098735 A1 | 7/2015 |

* cited by examiner

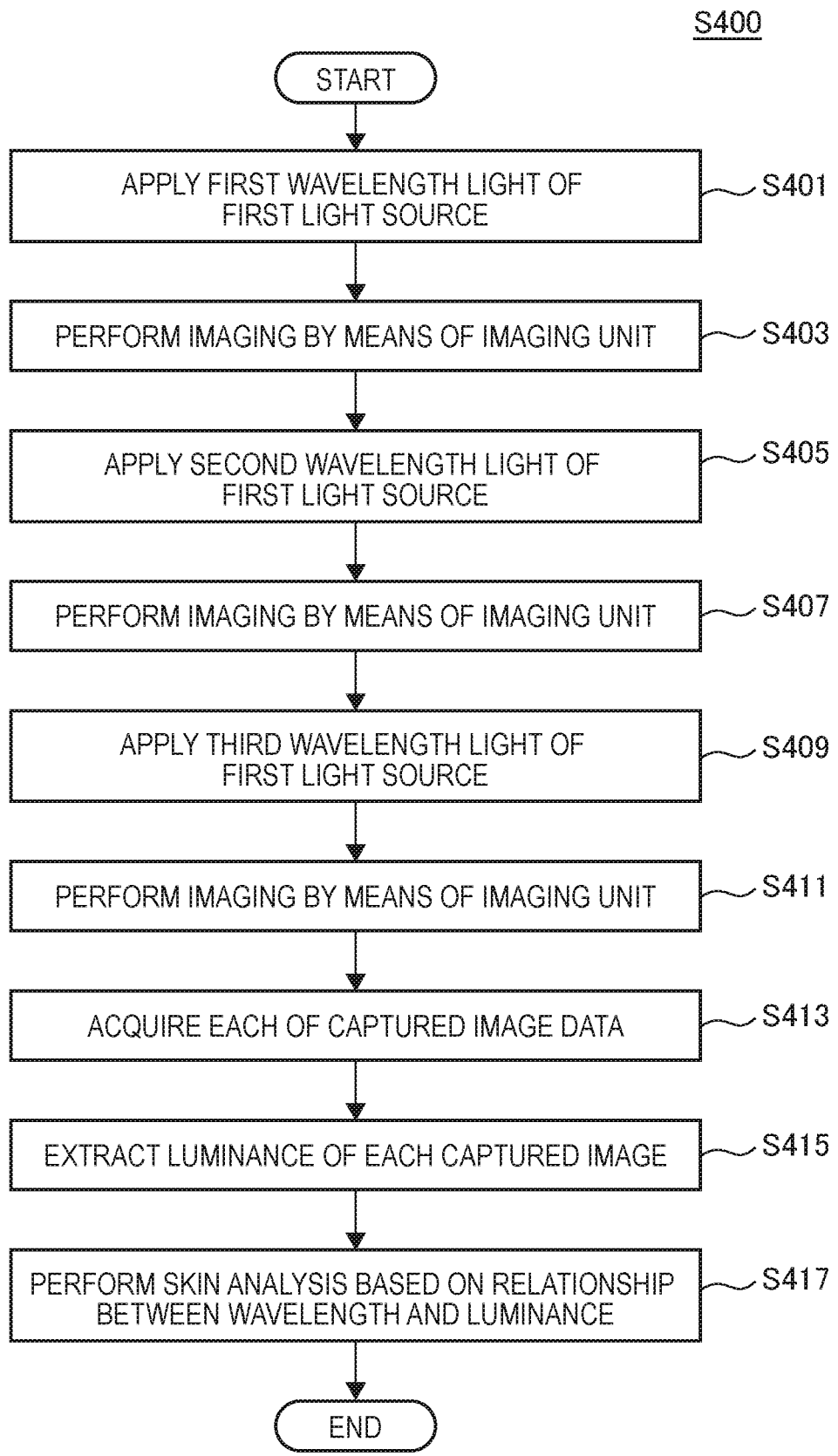

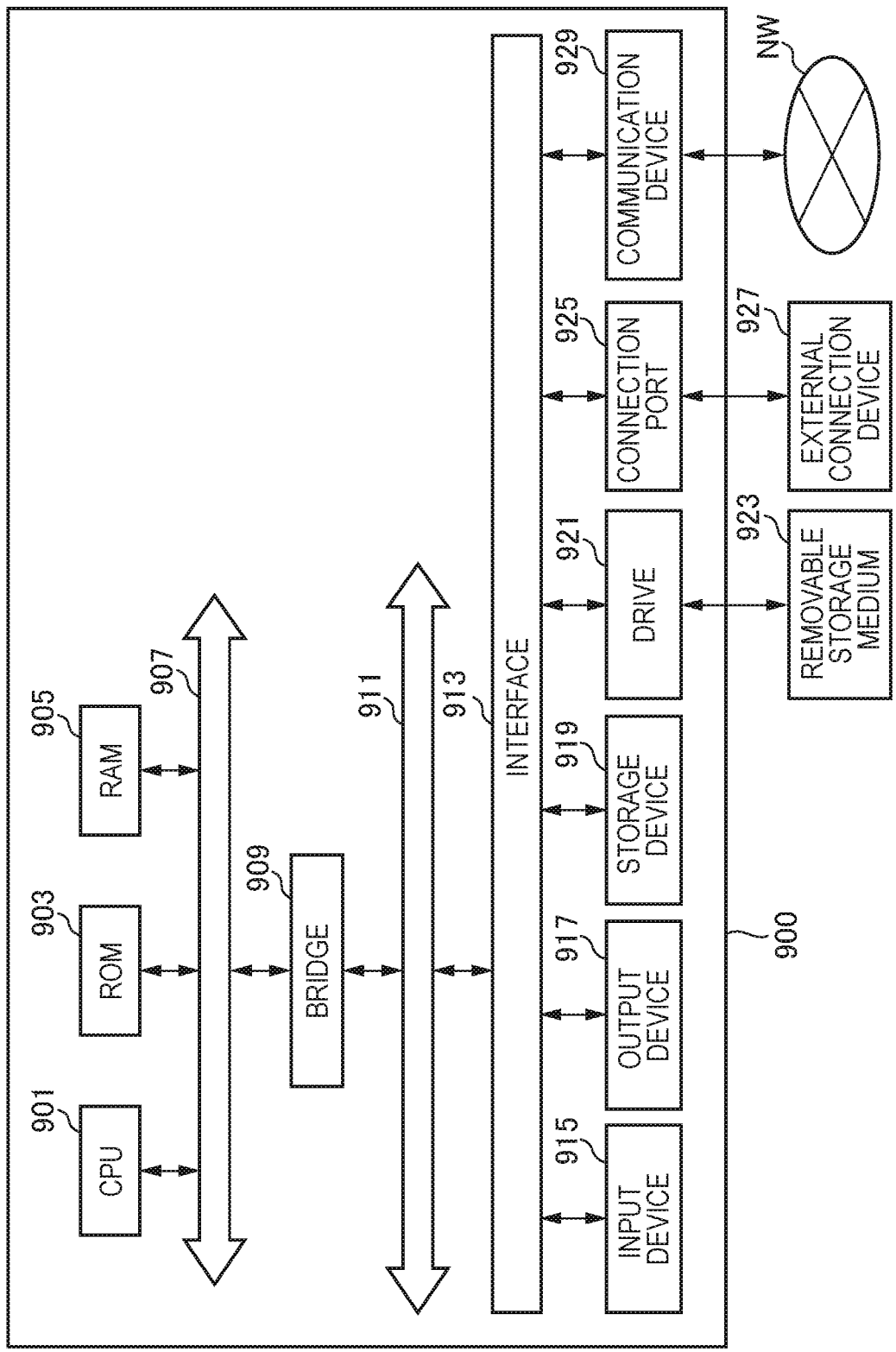

IMAGING APPARATUS, AUTHENTICATION PROCESSING APPARATUS, IMAGING METHOD, AUTHENTICATION PROCESSING METHOD

CROSS REFERENCE TO RELATED APPLICATIONS

This application is a U.S. National Phase of International Patent Application No. PCT/JP2017/005015 filed on Feb. 10, 2017, which claims priority benefit of Japanese Patent Application No. JP 2016-091816 filed in the Japan Patent Office on Apr. 28, 2016. Each of the above-referenced applications is hereby incorporated herein by reference in its entirety.

TECHNICAL FIELD

The present disclosure relates to an imaging apparatus, an authentication processing apparatus, an imaging method, an authentication processing method, and a program.

BACKGROUND ART

Biometric authentication, which is personal authentication utilizing living body information that is information inherent to a living body, is becoming performed in association with the evolution of information processing technology. As biometric authentication, for example, fingerprint authentication and vein authentication are known.

An authentication method in which two or more patterns such as a fingerprint pattern and a vein pattern are used in order to further enhance the accuracy of biometric authentication is proposed. For example, Patent Literature 1 below discloses a technology in which a plurality of pieces of authentication such as fingerprint authentication and vein authentication are performed by a single device.

CITATION LIST

Patent Literature

Patent Literature 1: JP 2008-297230A

DISCLOSURE OF INVENTION

Technical Problem

However, in the biometric authentication apparatus disclosed in Patent Literature 1 above, illumination devices used for the pieces of authentication are provided in the up and down directions of a living body, and hence it has been difficult to downsize the casing of the biometric authentication apparatus. Thus, the place, position, etc. where the biometric authentication apparatus can be installed have been limited. Therefore, the occasion when biometric authentication using the biometric authentication apparatus can be caused to be applied has been limited. Hence, convenience has not been high for users who want to use complex biometric authentication.

Thus, the present disclosure proposes a new and improved imaging apparatus, a new and improved authentication processing apparatus, a new and improved imaging method, a new and improved authentication processing method, and a new and improved program capable of achieving biometric authentication that is excellent in convenience and has high accuracy.

Solution to Problem

According to the present disclosure, there is provided an imaging apparatus including: a first light guide plate having a mounting surface including a mounting region where a part of a living body is to be mounted; a second light guide plate provided on the mounting surface excluding the mounting region; at least one first light source provided on an edge portion of the first light guide plate and configured to radiate first irradiation light of a prescribed wavelength to an interior of the first light guide plate; at least one second light source provided on an edge portion of the second light guide plate and configured to radiate second irradiation light of a prescribed wavelength to an interior of the second light guide plate; and an imaging unit placed on a side of a surface of the first light guide plate on an opposite side to the second light guide plate and configured to image light coming from a surface of the part of the living body.

In addition, according to the present disclosure, there is provided an authentication processing apparatus including: an imaging apparatus including a first light guide plate having a mounting surface including a mounting region where a part of a living body is to be mounted, a second light guide plate provided on the mounting surface excluding the mounting region, at least one first light source provided on an edge portion of the first light guide plate and configured to apply first irradiation light of a prescribed wavelength to an interior of the first light guide plate, at least one second light source provided on an edge portion of the second light guide plate and configured to apply second irradiation light of a prescribed wavelength to an interior of the second light guide plate, and an imaging unit placed on a side of a surface of the first light guide plate on an opposite side to the second light guide plate and configured to image light coming from a surface of the part of the living body and generate a captured image; and an information processing apparatus including a processing unit configured to perform processing regarding the living body including at least biometric authentication on a basis of the captured image generated in a state where the part of the living body is mounted on the mounting region.

In addition, according to the present disclosure, there is provided an imaging method including: applying first irradiation light of a prescribed wavelength from an edge portion of a first light guide plate having a mounting surface including a mounting region where a part of a living body is to be mounted, to an interior of the first light guide plate, in a state where the part of the living body is caused to be mounted on the mounting region; applying second irradiation light of a prescribed wavelength from an edge portion of a second light guide plate provided on the mounting surface excluding the mounting region, to an interior of the second light guide plate, in a state where the part of the living body is caused to be mounted on the mounting region; and imaging light coming from a surface of the part of the living body, from a side of a surface of the first light guide plate on an opposite side to the second light guide plate, while applying at least one of the first irradiation light or the second irradiation light.

In addition, according to the present disclosure, there is provided an authentication processing method including: applying first irradiation light of a prescribed wavelength from an edge portion of a first light guide plate having a mounting surface including a mounting region where a part of a living body is to be mounted, to an interior of the first light guide plate, in a state where the part of the living body is caused to be mounted on the mounting region; applying second irradiation light of a prescribed wavelength from an edge portion of a second light guide plate provided on the mounting surface excluding the mounting region, to an interior of the second light guide plate, in a state where the part of the living body is caused to be mounted on the mounting region; imaging light coming from a surface of the part of the living body, from a side of a surface of the first light guide plate on an opposite side to the second light guide plate, while applying at least one of the first irradiation light or the second irradiation light, and generating a captured image; and performing processing regarding the living body including at least biometric authentication on a basis of the generated captured image.

In addition, according to the present disclosure, there is provided a program for causing a computer to execute a processing function of performing processing regarding a living body including at least biometric authentication on a basis of a captured image generated in a state where a part of the living body is mounted on a mounting region, the computer being capable of communicating with an imaging apparatus including a first light guide plate having a mounting surface including the mounting region where the part of the living body is to be mounted, a second light guide plate provided on the mounting surface excluding the mounting region, at least one first light source provided on an edge portion of the first light guide plate and configured to apply first irradiation light of a prescribed wavelength to an interior of the first light guide plate, at least one second light source provided on an edge portion of the second light guide plate and configured to apply second irradiation light of a prescribed wavelength to an interior of the second light guide plate, and an imaging unit placed on a side of a surface of the first light guide plate on an opposite side to the second light guide plate and configured to image light coming from a surface of the part of the living body and generate the captured image.

Advantageous Effects of Invention

As described above, according to the present disclosure, biometric authentication that is excellent in convenience and has high accuracy can be achieved.

Note that the effects described above are not necessarily limitative. With or in the place of the above effects, there may be achieved any one of the effects described in this specification or other effects that may be grasped from this specification.

BRIEF DESCRIPTION OF DRAWINGS

FIG. 18 is a flow chart showing an example of a flow of skin analysis processing by the authentication processing apparatus according to the embodiment.

FIG. 19 is a block diagram showing a hardware configuration example of an information processing apparatus according to an embodiment of the present disclosure.

MODE(S) FOR CARRYING OUT THE INVENTION

Figure 1:
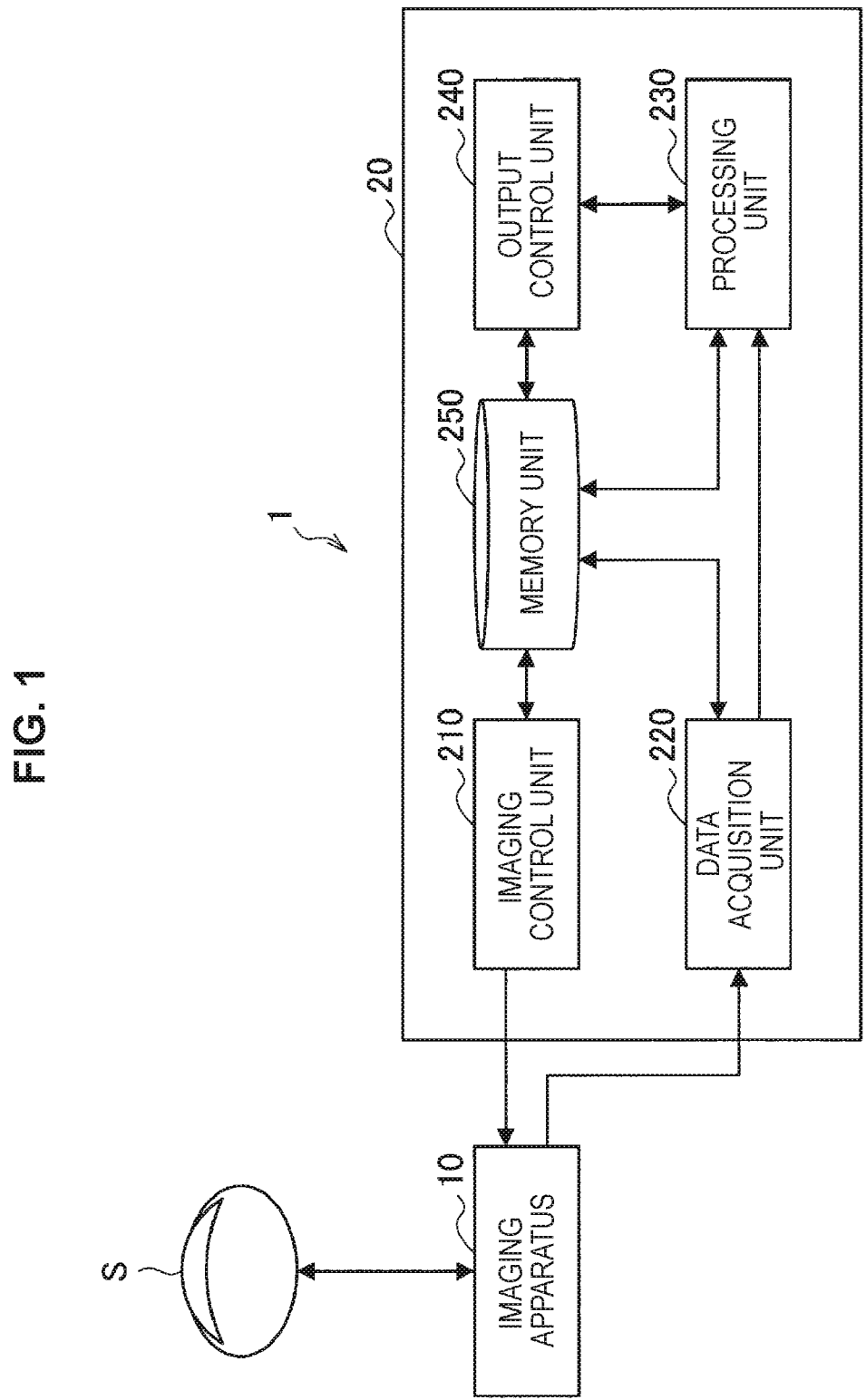
FIG. 1 is a block diagram showing a rough configuration of an authentication processing apparatus according to a first embodiment of the present disclosure.

Hereinafter, (a) preferred embodiment(s) of the present disclosure will be described in detail with reference to the appended drawings. Note that, in this specification and the appended drawings, structural elements that have substantially the same function and structure are denoted with the same reference numerals, and repeated explanation of these structural elements is omitted.

Note that the description is given in the following order.

1. First Embodiment 1.1. Overview
1.2. Imaging apparatus
1.3. Information processing apparatus
1.4. Flows of processing
1.5. Supplements
1.6. Sub-conclusion
2. Second embodiment (configuration including analysis processing)
2.1. Configuration example
2.2. Flows of processing
2.3. Sub-conclusion
3. Hardware configuration example
4. Conclusions

1. First Embodiment

1.1. Overview

FIG. 1 is a block diagram showing a rough configuration of an authentication processing apparatus 1 according to a first embodiment of the present disclosure. As shown in FIG. 1, the authentication processing apparatus 1 includes an imaging apparatus 10 and an information processing apparatus 20. The imaging apparatus 10 and the information processing apparatus 20 are connected directly or indirectly by various wired or wireless networks.

Imaging Apparatus

The imaging apparatus 10 according to the present embodiment images light coming from a surface of a sample S that is an imaging object. Specifically, the imaging apparatus 10 radiates light having a prescribed wavelength (irradiation light) to the sample S, and images light coming from a surface of the sample S in a state where the sample S is irradiated with irradiation light.

Here, the sample S in the present embodiment is a part of a living body, for example. More specifically, as shown in FIG. 1, the sample S may be a finger of a user. In this case, the surface of the sample S corresponds to a portion of the inner surface of the finger of the user, and the living body corresponds to the user. In the following, a finger of a user that is the sample S is described as an example of a part of a living body; however, the sample S is not limited to this example. For example, the sample S may be a part (specifically, an arm, a leg, the head, or the trunk) other than the fingers of a human body. In this case, the imaging apparatus 10 images light coming from the skin of the part, for example.

The irradiation light mentioned above is scattered on the surface or in the interior of the sample S. The imaging apparatus 10 images these scattered lights, and generates a captured image regarding the sample S. The captured image is a captured image corresponding to a living body structure or a living body component related to the finger of the user, for example. More specifically, the captured image may be a captured image including a fingerprint pattern or a vein pattern related to the finger of the user, for example.

Further, the imaging apparatus 10 includes a communication device that can communicate with the information processing apparatus 20. The captured image generated by the imaging apparatus 10 is transmitted to the information processing apparatus 20. Note that the captured image to be transmitted to the information processing apparatus 20 may be a series of captured images that are consecutively generated by performing imaging over time, such as moving images.

Information Processing Apparatus

The information processing apparatus 20 according to the present embodiment is an apparatus having functions related to various pieces of information processing. Specifically, the information processing apparatus 20 controls the imaging apparatus 10 to cause the imaging apparatus 10 to generate a captured image, and acquires the captured image. Then, the information processing apparatus 20 performs image processing on the captured image, and performs processing related to biometric authentication by using the captured image after image processing.

The information processing apparatus 20 may be obtained using any apparatus as long as it is an apparatus including a processing circuit and a communication device. For example, the information processing apparatus 20 may be obtained using a personal computer (PC), a tablet, a smartphone, a game machine, a smart watch, a wearable device, etc.

Note that detailed configurations and various functions of the imaging apparatus 10 and the information processing apparatus 20 according to the present embodiment are described later.

The authentication processing apparatus 1 according to the present embodiment includes the imaging apparatus 10 and the information processing apparatus 20 that are provided integrally. For example, the authentication processing apparatus 1 according to the present embodiment may be a configuration in which the imaging apparatus 10 and the information processing apparatus 20 are incorporated in a single casing.

Further, the authentication processing apparatus (authentication system) according to the present embodiment may be a configuration in which the imaging apparatus 10 and the information processing apparatus 20 are independent of each other. In this case, processing by the information processing apparatus 20 such as the control of the imaging apparatus 10 and the acquisition of a captured image from the imaging apparatus 10 is performed via communication devices included in the imaging apparatus 10 and the information processing apparatus 20.

Such an authentication processing apparatus 1 may be used for all devices or apparatuses in which personal authentication is required. For example, the authentication processing apparatus 1 may be provided not only in an information processing terminal such as a PC, a tablet, a mobile phone, a smartphone, a game machine, a smart watch, or a wearable device described above, but also in a transport apparatus such as a two-wheeled vehicle or an automobile, a home electrical appliance such as a television, an audio apparatus, or a refrigerator, a locking device such as a lock, a time recorder, an automatic service machine such as a vending machine or an automated teller machine (ATM), or other devices etc. in which personal authentication is required.

Further, for example, a configuration in which only the imaging apparatus 10 is provided in any of the various devices described above in which personal authentication is required is possible. In this case, processing related to biometric authentication or the like may be performed by the information processing apparatus 20 that is provided separately from the imaging apparatus 10 and that can communicate with the imaging apparatus 10.

Hereinbelow, the imaging apparatus 10 and the information processing apparatus 20 included in the authentication processing apparatus 1 are described.

1.2. Imaging Apparatus

Configuration Example

Figure 2:
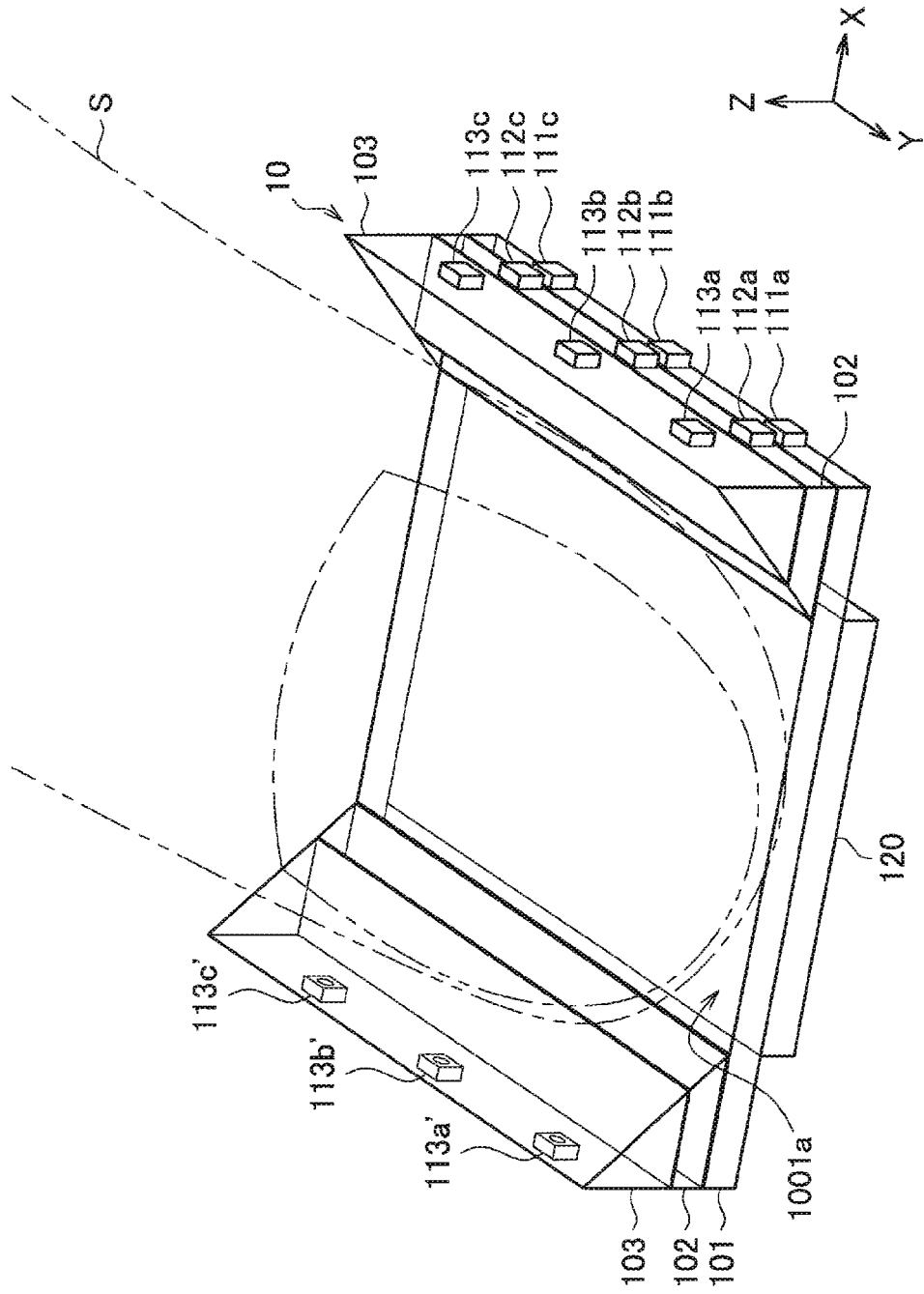
FIG. 2 is a perspective view showing a configuration example of an imaging apparatus according to the embodiment.
Figure 3:
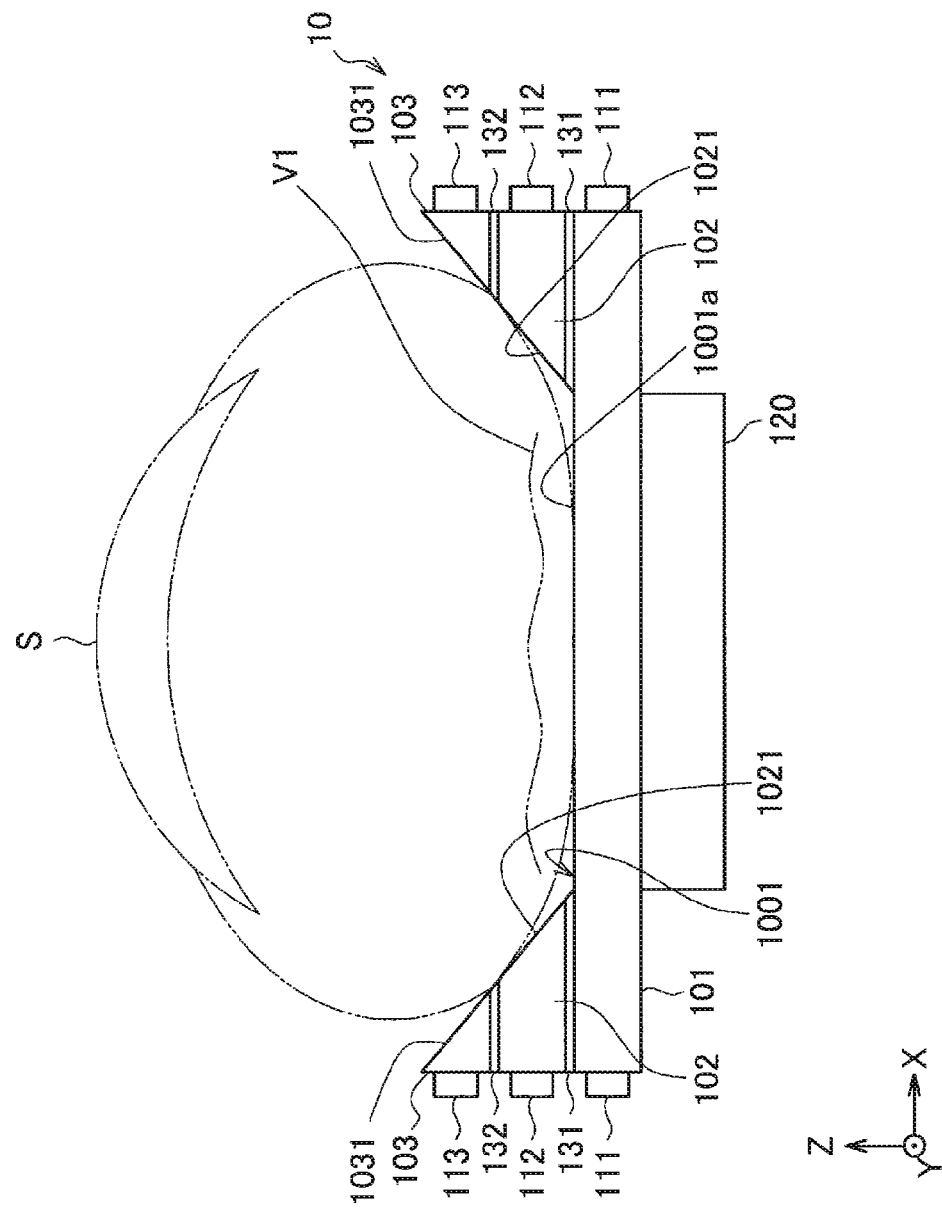
FIG. 3 is a front view showing the configuration example of the imaging apparatus according to the embodiment.

FIG. 2 is a perspective view showing a configuration example of the imaging apparatus 10 according to the present embodiment. Further, FIG. 3 is a front view showing the configuration example of the imaging apparatus 10 according to the present embodiment. Note that, as shown in FIG. 2 and FIG. 3, in the following a description is given on the assumption that an X-axis direction is the width direction of the imaging apparatus 10, a Y-axis direction is the direction of mounting of a finger S, and a Z-axis direction is the up and down direction (the positive direction is the up direction) of the imaging apparatus 10.

Referring to FIG. 2 and FIG. 3, the imaging apparatus 10 according to the present embodiment mainly includes a first light guide plate 101, second light guide plates 102, third light guide plates 103, first light sources 111 (111a to 111c), second light sources 112 (112a to 112c), third light sources 113 (113a to 113c), and an imaging unit 120. Further, the imaging apparatus 10 according to the present embodiment may further include first light blocking bodies 131 and second light blocking bodies 132.

Note that, unless otherwise distinguished, in the following description the first light guide plate 101, the second light guide plate 102, and the third light guide plate 103, and the first light source 111, the second light source 112, and the third light source 113 may be referred to as each light guide plate and each light source, respectively.

Light Guide Plate

The first light guide plate 101, the second light guide plate 102, and the third light guide plate 103 are light guide plates that guide irradiation lights radiated from the first light source 111, the second light source 112, and the third light source 113 to the inside, respectively.

A mounting region 1001a for mounting the finger S is provided on one surface (a mounting surface 1001) of the first light guide plate 101. Further, although as shown in FIG. 2 the mounting region 1001a according to the present embodiment is provided from one end to the other end of the first light guide plate 101 in the mounting direction, the size and shape of the mounting region 1001a are not limited to this example. For example, the size of the mounting region 1001a may be set to such a degree that a fingerprint pattern of the finger S can be acquired, as appropriate. Further, the mounting region 1001a may be a closed region having an arbitrary shape such as a circle, an ellipse, a substantially rectangular shape, or a substantially trapezoidal shape, or may be a region including, as an edge line, the whole or part of one end of the first light guide plate 101 in the mounting direction.

The second light guide plate 102 is provided on a surface of the mounting surface 1001 of the first light guide plate 101 other than the mounting region 1001a. In this event, as shown in FIG. 2 and FIG. 3, the second light guide plate 102 may be provided on each of the upper sides of both end portions in the X-axis direction of the first light guide plate 101. The number of second light guide plates 102 installed is not particularly limited, and may be set on the basis of the size and shape of the mounting region 1001a, the amount of irradiation light from the second light source 112, which amount is required in accordance with the amount of scattered light to be injected into the imaging unit 120 described later, etc., as appropriate.

Further, as shown in FIG. 2 and FIG. 3, the third light guide plate 103 may be further provided on the upper surface of the second light guide plate 102. For example, as shown in FIG. 2 and FIG. 3, in a case where two second light guide plates 102 are provided on the upper sides of both end portions in the X-axis direction of the first light guide plate 101, the third light guide plate 103 may be provided on the upper surface of each of the second light guide plates 102.

The size in the in-plane direction of the first light guide plate 101 is not particularly limited, and may be set in accordance with, for example, the structures of various terminals etc. to be equipped with the imaging apparatus 10, as appropriate. Further, the size in the in-plane direction of the first light guide plate 101 may be set in accordance with the size of a part of a living body that is an imaging object, as appropriate.

The size and shape in the in-plane direction of the second light guide plate 102 may be set on the basis of, for example, the size and shape of the mounting region 1001a, the amount of irradiation light from the second light source 112, which amount is required in accordance with the amount of scattered light to be injected into the imaging unit 120 described later, etc., as appropriate. For example, in the example shown in FIG. 2 and FIG. 3, the second light guide plate 102 is provided so as to cover a surface other than the mounting region 1001a of the mounting surface 1001 of the first light guide plate 101; however, the present technology is not limited to this example. For example, the second light guide plate 102 may be provided on at least part of the mounting surface 1001 other than the mounting region 1001a. Similarly, the size and shape in the in-plane direction of the third light guide plate 103 may be set on the basis of, for example, the size and shape of the second light guide plate 102, the amount of irradiation light from the third light source 113, which amount is required in accordance with the amount of scattered light to be injected into the imaging unit 120, etc., as appropriate.

The thicknesses of the first light guide plate 101, the second light guide plate 102, and the third light guide plate 103 are not particularly limited, but the thicknesses are preferably as small as possible. For example, the thickness of the first light guide plate 101 may be set in accordance with the deterioration of the first light guide plate 101 or the influence on the optical paths of irradiation light and scattered light propagating through the interior of the first light guide plate 101, both of which factors are caused by warpage due to the mounting of the finger S, the amount of irradiation light from the first light source 111 to be applied to the interior of the first light guide plate 101, etc., as appropriate. Further, the thicknesses of the second light guide plate 102 and the third light guide plate 103 may be set in accordance with the amounts of the respective irradiation lights to be applied to the interiors of the respective light guide plates, etc., as appropriate.

Note that, referring to FIG. 3, a side surface 1021 of the second light guide plate 102 on the side adjacent to the mounting region 1001a may be inclined with respect to the Z-axis direction toward the outside in the width direction. Thereby, the inner surface of the finger S is less likely to be caught in an end portion of the side surface 1021 of the second light guide plate 102, and therefore it becomes easier for the finger S to be caused to be mounted on the mounting region 1001a. Further, the shape of the side surface 1021 is not limited to the example shown in FIG. 3. For example, the side surface 1021 may be a concave curved surface so as to run along the surface of the finger S. The angle of inclination of the side surface 1021, the magnitude of the curvature in a case where the side surface 1021 is a curved surface, etc. are set in accordance with the size, material, etc. of each light guide plate, as appropriate. Further, the cross-sectional shape in the Y-axis direction of the second light guide plate 102 may be a substantially rectangular shape. Note that the inclination etc. may be similarly provided also on a side surface 1031 of the third light guide plate 103 adjacent to the side surface 1021, as appropriate. Further, although in the example shown in FIG. 3 the cross-sectional shape in the Y-axis direction of the third light guide plate 103 is a triangle, the cross-sectional shape is not limited to this example, and may be a substantially rectangular shape, a substantially trapezoidal shape, etc., for example.

As the material of each light guide plate, a resin such as an acrylic, urethane rubber, silicon rubber, a polyurethane, a polycarbonate, or a cycloolefin-based resin, or various optical materials such as glass may be used.

Note that the first light guide plate 101 and the second light guide plate 102 (and the third light guide plate 103) may contain optical materials having optical characteristics different from each other. Although details are described later, for example, the first light guide plate 101 may contain an optical material in which the wavelength of irradiation light radiated from the first light source 111 (a first irradiation light) and the wavelength of irradiation light radiated from the second light source 112 (a second irradiation light) are included in a passband. In this case, the second light guide plate 102 may contain an optical material in which the wavelength of the first irradiation light is included in a stopband. Thereby, scattered light resulting from the first irradiation light and the second irradiation light can be transmitted through the first light guide plate 101 and injected into the imaging unit 120, and yet the occurrence of what is called crosstalk in which the first irradiation light leaked out from the first light guide plate 101 leaks into the second light guide plate 102 can be suppressed.

Light Source

The first light source 111, the second light source 112, and the third light source 113 radiate lights of prescribed wavelengths (irradiation lights) to the interiors of the first light guide plate 101, the second light guide plate 102, and the third light guide plate 103, respectively.

The first light source 111 is placed on an edge portion of the first light guide plate 101 (a side peripheral surface of the first light guide plate 101), for example. In the example shown in FIG. 2 and FIG. 3, the first light source 111 is placed on each of both end surfaces in the X-axis direction of the first light guide plate 101. Similarly, the second light source 112 is placed on an edge portion of the second light guide plate 102 (among the side peripheral surfaces of the second light guide plate 102, a surface on a side not adjacent to the mounting region 1001a), and the third light source 113 is placed on an edge portion of the third light guide plate 103. The placement position of each light source is not limited to, for example, the example shown in FIG. 2 and FIG. 3 as long as an appropriate amount of the respective irradiation light can be radiated toward the mounting region 1001a and a space above the mounting region 1001a.

Further, the number of light sources of each kind placed on the respective light guide plate is not particularly limited. For example, in the example shown in FIG. 2, a plurality of first light sources 111a to 111c are placed on the first light guide plate 101. This similarly applies to second light sources 112a to 112c and third light sources 113a to 113c. The placement method in a case where a plurality of light sources of each kind are provided is not particularly limited; for example, light sources of each kind may be placed at fixed intervals as shown in FIG. 2, or light sources of each kind may be juxtaposed adjacently. Further, for example as shown in FIG. 2, in a case where two third light guide plates 103 are juxtaposed along the X-axis direction, third light sources 113 (third light sources 113a to 113c and third light sources 113a' to 113c') may be provided on edge portions of the respective light guide plates.

Here, the wavelength of irradiation light radiated by each light source is described. The wavelength of irradiation light radiated by each light source is selected from, for example, wavelengths falling within the range between the visible light band to the near-infrared band, and may be set in accordance with a living body component, a living body structure, etc. of interest, as appropriate. Types of irradiation light, wavelengths corresponding to the respective types of irradiation light, and examples of living body components, living body structures, etc. serving as the imaging object (the measurement object) based on irradiation light are shown in Table 1 below.

TABLE 1

| Kind | Wavelength (nm) | Examples of imaging object (measurement object) |
| --- | --- | --- |
| Near-infrared light | 940 | Veins; melanin; the thickness of subcutaneous fat |
| Red light | 660 | The nature (clearness) of the skin; arteries (pulsation); melanin |
| Green light | 570 | Fingerprints; arteries (pulsation) |

For example, an irradiation light with a wavelength of around 940 nm, such as near-infrared light, has the feature of having high transmissivity to bodily tissues and on the other hand being absorbed in hemoglobin in blood in veins (reduced hemoglobin). Hence, for example, if a finger irradiated with near-infrared light is imaged, veins distributed in the interior of the finger appear as shadows in the captured image. These shadows can be acquired as a vein pattern (the mechanism thereof is described later). Further, by applying the near-infrared light, findings regarding blood components regarding reduced hemoglobin or melanin pigment can be obtained.

In addition to the above, by applying near-infrared light, findings regarding fat existing in subcutaneous tissues (for example, the thickness of subcutaneous fat, etc.) can be obtained. Near-infrared light applied from the surface of the skin can arrive at a subcutaneous fat layer and a muscle layer. In general, in the wavelength region of near-infrared light, a muscle tends to absorb near-infrared light (an absorber), and fat tends to scatter near-infrared light (a scatterer). Hence, when near-infrared light is applied from the surface of the skin, if the thickness of subcutaneous fat is large, irradiation light is scattered farther in the fat, and the scattering area is large. That is, the scattering distance of irradiation light becomes longer in proportion to the thickness of subcutaneous fat. Therefore, the thickness of subcutaneous fat can be estimated by measuring the distance from the light source of irradiation light to the emission position of scattered light that is scattered from the surface of the skin (corresponding to a scattering distance). Further, in a case where the thickness of subcutaneous fat is large, the intensity of scattered light (internally reflected light) emitted from the surface of the skin is increased. Therefore, the thickness of subcutaneous fat can be estimated also by measuring the intensity (intensity distribution) of internally reflected light relative to the intensity of irradiation light applied from the surface of the skin.

Further, for example, an irradiation light with a wavelength of around 660 nm, such as red light, has the feature of having a certain level of high transmissivity to bodily tissues and on the other hand being absorbed in hemoglobin in blood in arteries (oxygenated hemoglobin). Hence, for example, by applying red light to an outer layer of a finger and acquiring the reflectance of the red light, findings regarding the nature of the skin (for example, the clearness of the skin) can be obtained. Similarly to the thickness of subcutaneous fat described above, these findings can be obtained by utilizing the scattering distance and/or the intensity of scattered light (internally reflected light) that, when red light is applied from the surface of the skin, is scattered in the interior of the skin and is emitted from the surface of the skin. In general, it is said, if the clearness of the skin is high, the ratio of the amount of scattered light emitted from the skin to irradiation light injected in the skin is high, and there is a state of being emitted uniformly from the entire skin. Therefore, the clearness of the skin can be estimated by measuring the scattering distance and/or the intensity (intensity distribution) of internally reflected light. Further, by applying red light to the interior of a finger and acquiring the absorptance of the red light over time, time-series changes in the capacity of the blood vessels of arteries (a pulse wave) can be grasped. That is, the pulsation can be measured. Further, by applying the red light, findings regarding blood components regarding oxygenated hemoglobin or melanin pigment can be obtained. Note that processing using findings regarding melanin pigment is described later.

Further, for example, an irradiation light with a wavelength of around 570 nm, such as green light, has the feature of having low transmissivity to bodily tissues and being absorbed in oxygenated hemoglobin in blood in arteries. Hence, for example, a fingerprint pattern of a finger can be obtained by using the green light (the mechanism thereof is described later). Further, by applying green light to the interior of a finger and acquiring the absorptance of the green light over time, time-series changes in the capacity of the blood vessels of arteries (a pulse wave) can be grasped. That is, the pulsation can be measured.

Note that, although details are described later, a fingerprint pattern is obtained by imaging scattered light at the contact interface between the mounting region 1001a of the first light guide plate 101 and the finger S. Hence, when acquiring a fingerprint pattern, the light is not limited to green light described above, and an irradiation light falling within the wavelength band of visible light, such as blue color, may be used as appropriate.

Further, although not described in Table 1 above, findings regarding glucose can be obtained by radiating light of a wavelength of 1400 nm to 2200 nm, for example. Further, in the measurement of pulsation, light having a wavelength in the near-infrared light region to the infrared light region may be used, as well as light having the wavelengths described above.

Note that the various wavelengths described above are only examples, and the light radiated by each light source of the imaging apparatus 10 according to the present embodiment is not limited to the above examples.

As described above, the wavelengths of the irradiation lights radiated by the first light source 111, the second light source 112, and the third light source 113 are set in accordance with the imaging object or the measurement object that is of interest, as appropriate. Although details are described later, for example, the wavelength may be different between the irradiation light from the first light source 111 (the first irradiation light) and the irradiation light from the second light source 112 (the second irradiation light). Thereby, a first captured image resulting from the first irradiation light and a second captured image resulting from the second irradiation light can be generated by using one imaging apparatus 10. That is, biometric authentication processing etc. using the first captured image and the second captured image can be performed in the information processing apparatus 20 described later.

Further, in a case where a plurality of first light sources 111a to 111c are provided as shown in FIG. 2, the wavelengths of the irradiation lights radiated from the first light sources 111a to 111c may be the same, or may be different from each other. Similarly, also the wavelengths of the irradiation lights radiated from the second light sources 112a to 112c and the third light sources 113a to 113c may be the same, or may be different from each other.

Further, each light source may radiate irradiation light continuously, or may radiate irradiation light intermittently. For example, by radiating irradiation light intermittently, light that is detected in a time period other than the radiation timing can be considered as light influenced by external light. Thus, by imaging light that is detected in a time period other than the radiation timing, the use of a captured image in a case where the influence of very large external light is detected can be invalidated in the information processing apparatus 20 described later.

As such a light source of each kind, for example, a light emitting diode (LED) is used. The LED used as a light source of each kind may be one that radiates an irradiation light of a single wavelength, or may be one that radiates an irradiation light of a plurality of wavelengths, such as a full-color LED. Further, a small-sized laser may be used as a light source of each kind.

Further, the radiation timing of irradiation light, the intensity of irradiation light, etc. in each light source are controlled by an imaging control unit 210 of the information processing apparatus 20 described later. Specific control by the imaging control unit 210 is described later.

Imaging Unit

The imaging unit 120 according to the present embodiment images light coming from a surface of a finger C. For example, the imaging unit 120 images scattered light that is injected by irradiation lights radiated from the light sources being scattered on the surface or in the interior of the finger C.

Figure 4:
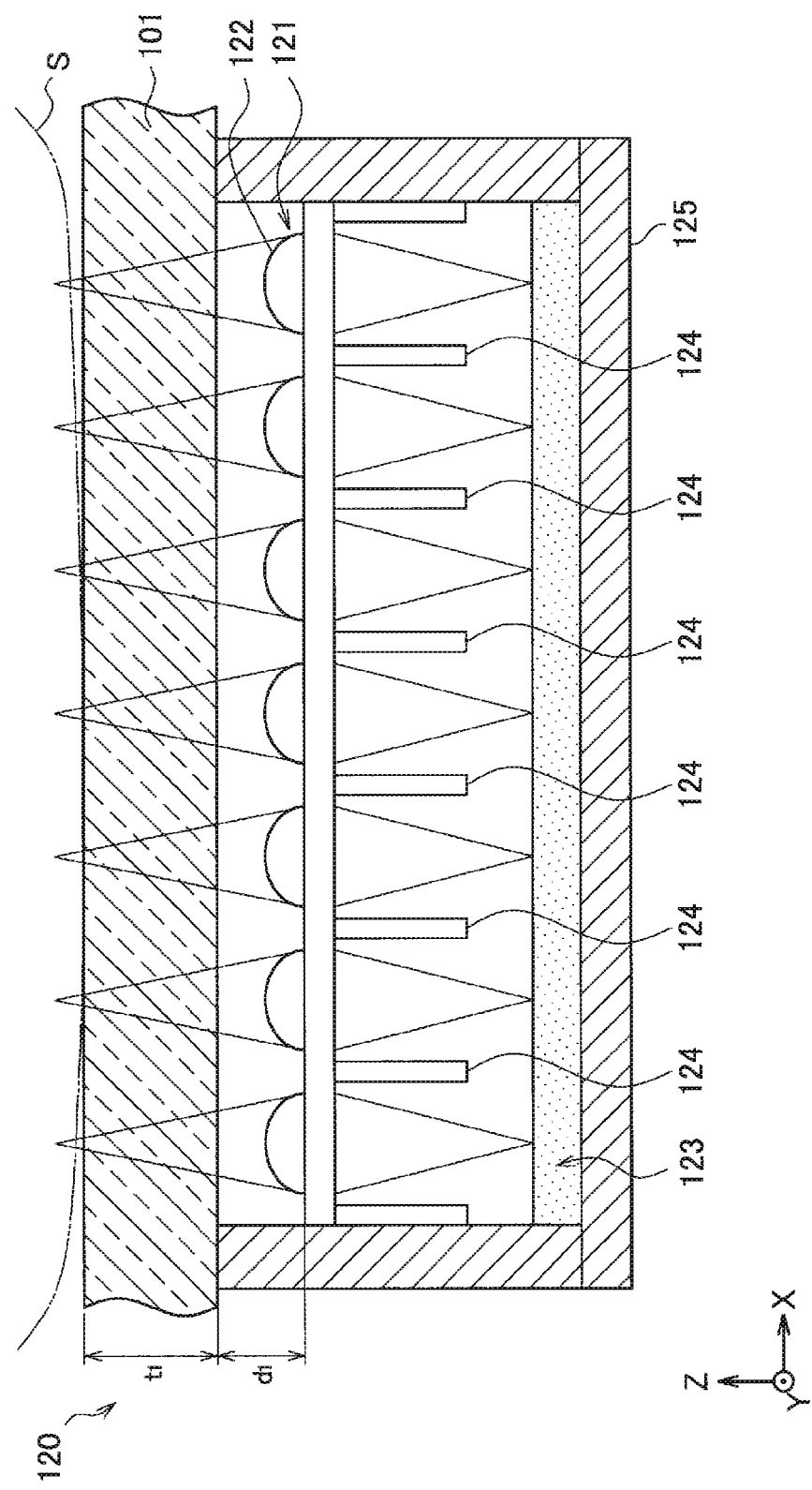
FIG. 4 is a diagram for describing a configuration example of an imaging unit according to the embodiment.

Such an imaging unit 120 may include, for example, an imaging element 123 provided with an optical system including a microlens array (MLA) 121, like that shown in FIG. 4. FIG. 4 is a diagram for describing a configuration example of the imaging unit 120 according to the present embodiment. Referring to FIG. 4, the imaging unit 120 includes, in the interior of a casing 125, the microlens array 121 including a plurality of microlenses 122, the imaging element 123, and a plurality of light blocking bodies 124. Note that, although not illustrated in FIG. 4, light blocking bodies for controlling the directivity of scattered light injected into the imaging unit 120 may be further provided on the upper side of the microlens array 121.

The microlens array 121 includes a plurality of microlenses 122 that are light receiving lenses. The microlenses 122 are arrayed in a lattice configuration on a prescribed substrate. The number and the arraying positions of arranged microlenses 122 are not particularly limited, and may be set in accordance with the size of a living body that is the imaging object and the size of the imaging element 123 described later, as appropriate.

Each microlens 122 guides scattered light injected in the microlens 122 to the imaging element 123. The microlens array 121 is a lens array having little curvature of field and having no distortion in the depth direction. Hence, a good captured image can be obtained by using such a microlens array 121.

Note that the depth of field of each microlens 122 included in the microlens array 121 is set such that a living body structure of interest is covered by the imaging apparatus 10 according to the present embodiment even in a case where the finger S exists at a close-up distance (for example, such that a depth range of several millimeters to a dozen or so millimeters from the surface of the finger is focused on).

More specifically, the focus position of each microlens 122 may be set so as to be a position of a vein layer in which veins V1 shown in FIG. 3, which exist near the surface of the finger S, exist. It is known that the skin of a human body has a three-layer structure of the cuticle layer, the dermis layer, and the subcutaneous tissue layer; the vein layer described above exists in the dermis layer. The dermis layer is a layer existing with a thickness of approximately 2 mm to 3 mm, from a position of approximately 0.1 mm to 0.3 mm from the surface of the finger. Therefore, although details are described later, scattered light from near the vein layer can be collected with good efficiency by setting the focus position of the microlens 122 to near such a position where the dermis layer exists (for example, a position of approximately 1.5 mm to 2.0 mm from the surface of the finger). Further, the focus position of the microlens 122 is not limited to the example described above, and is set as appropriate.

Note that it is preferable that the microlens array 121 according to the present embodiment be provided such that the thickness ti of the first light guide plate 101 is more than or equal to the separation distance di between the microlens array 121 and the first light guide plate 101. In a case where the thickness ti of the first light guide plate 101 is larger than the separation distance di, the strength of the first light guide plate 101 can be gained, and scattered light from the finger S can be prevented from being attenuated. Therefore, a more vivid captured image can be obtained for the imaging object.

Scattered light incident on the microlens array 121 is collected by the microlens 122, and is caused to form an image in the imaging element 123.

In order to control the directivity of scattered light transmitted through the microlens array 121, the light blocking body 124 is provided in a boundary portion between microlenses 122 adjacent to each other, on a surface of the microlens array 121 on the imaging element 123 side, as appropriate. Thereby, light incident on each microlens 122 can be separated from light incident on an adjacent microlens 122. Therefore, in the imaging apparatus 10 according to the present embodiment, some scattered lights collected in the imaging element 123 can be selected. Further, although not shown in FIG. 4, an aperture may be further provided in the boundary portion mentioned above.

By providing such a light blocking body 124 and such an aperture, the angle of incidence of light incident on each microlens 122 can be limited, and crosstalk between microlenses 122 of scattered light can be prevented. Further, by preventing crosstalk between microlenses 122, signals obtained from sensor pixels corresponding to some microlenses 122 among the plurality of microlenses 122 provided in the microlens array 121 (that is, signals corresponding to local positions in the imaging region) can be acquired. Thereby, the resolving power of the captured image generated by the imaging element 123 described later can be improved.

The imaging element 123 has an imaging surface on which a plurality of light receiving elements are arranged in a lattice configuration; and images scattered light that is formed as an image, and generates a captured image based on the scattered light. Further, the imaging element 123 outputs the generated captured image to the information processing apparatus 20.

The imaging element 123 may include, for example, an image sensor using a photodiode, a charge-coupled device (CCD), a complementary metal oxide semiconductor (CMOS), organic electro-luminescence (EL), a thin film transistor (TFT), or the like.

Note that, in the imaging element 123, at least one light receiving element may be placed for one microlens 122. That is, scattered light collected by one microlens 122 may be imaged by one or a plurality of light receiving elements. Further, the operating timing etc. of each light receiving element in the imaging element 123 are controlled by an imaging control unit 210 of the information processing apparatus 20 described later.

Hereinabove, the configuration example of the imaging unit 120 shown in FIG. 4 is described. Note that the imaging unit 120 according to the present embodiment is not limited to one including a microlens array 121 like that shown in FIG. 4. For example, the imaging unit 120 may have any configuration as long as light from the surface of the finger S, which is the imaging object, can be collected and can be caused to form an image in the imaging element. However, by the inclusion by the imaging unit 120 of an optical system including the microlens array 121, the size in the Z-axis direction (thickness) of the imaging unit 120 can be made as small as possible. That is, the imaging apparatus 10 can be downsized more, and the convenience of the authentication processing apparatus 1 is further improved.

Light Blocking Body

Furthermore, the imaging apparatus 10 according to the present embodiment may include the first light blocking body 131 and the second light blocking body 132. The first light blocking body 131 may be provided so as to be sandwiched between the first light guide plate 101 and the second light guide plate 102, for example. Further, the second light blocking body 132 may be provided so as to be sandwiched between the second light guide plate 102 and the third light guide plate 103. Further, each light blocking body may be provided in a region including at least the interface between the upper and lower light guide plates.

Each light blocking body is provided in order to prevent crosstalk of irradiation light propagating through the interior of each light guide plate. Each light blocking body includes a light blocking filter or the like, for example. The light blocking characteristics that these light blocking bodies can exhibit may be selected in accordance with, for example, the wavelength of irradiation light applied to the interior of each of the adjacent light guide bodies. For example, the first light blocking body 131 may have a light blocking characteristic of including the wavelengths of the first irradiation light and the second irradiation light as a stopband. Thereby, crosstalk of the first irradiation light to the second light guide plate 102 and crosstalk of the second irradiation light to the first light guide plate 101 can be suppressed. Further, the light blocking characteristics mentioned above may be selected in accordance with the passband of each light guide plate.

Hereinabove, a configuration example of the imaging apparatus 10 according to the present embodiment is described.

Operation Examples

Next, operation examples of the imaging apparatus 10 according to the present embodiment are described. In the following, examples in which captured images including a fingerprint pattern and a vein pattern of the finger S are acquired using the imaging apparatus 10 are described using FIG. 5 to FIG. 8. Note that the fingerprint pattern is acquired on the basis of the first irradiation light, and the vein pattern is acquired on the basis of the second irradiation light or a third irradiation light. Hence, it is preferable that the timing of radiation of the first irradiation light by the first light source 111 be different from the timing of radiation of the second irradiation light (or the third irradiation light) by the second light source 112 (or the third light source 113).

Acquisition of Fingerprint Pattern

Figure 5:
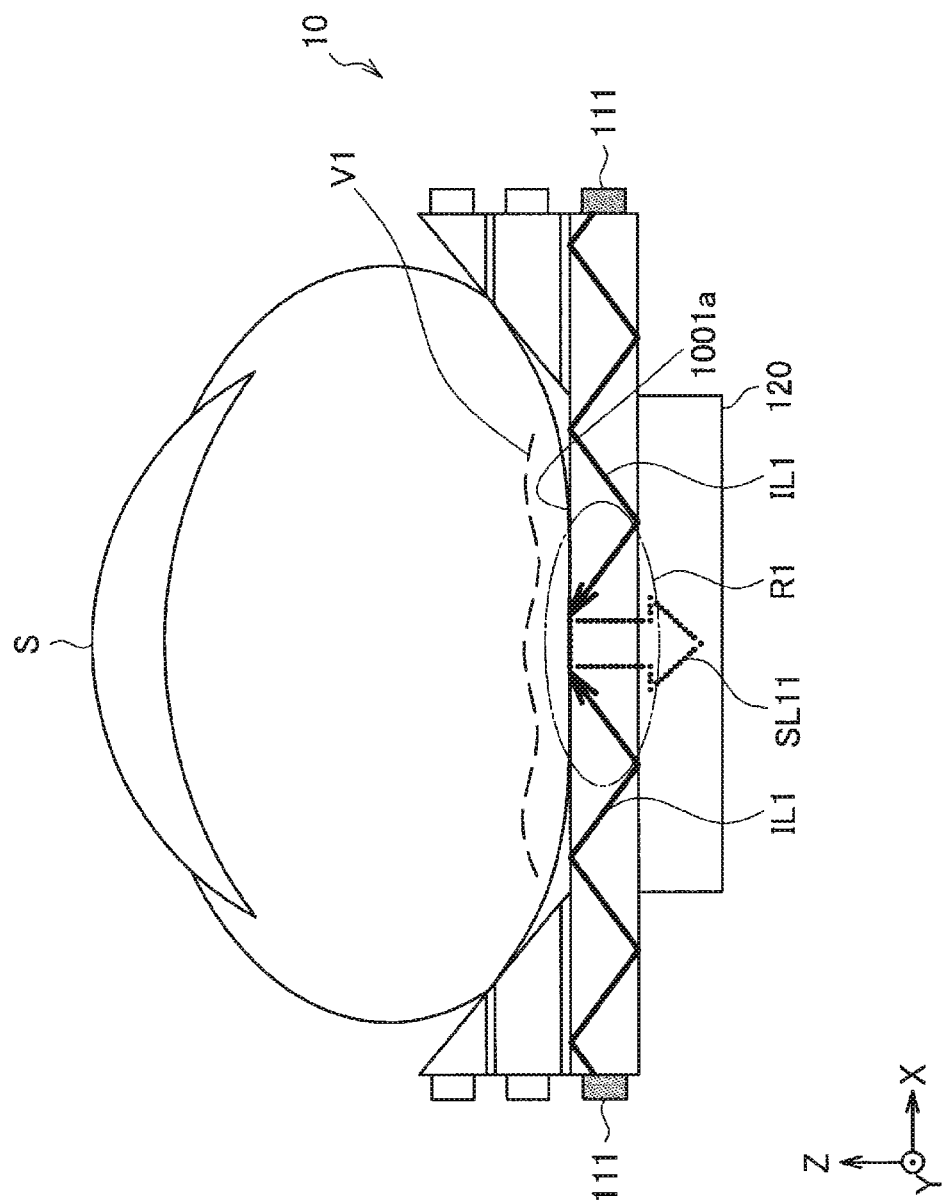
FIG. 5 is a diagram for describing an operation example of the imaging apparatus in acquisition of a fingerprint pattern.

FIG. 5 is a diagram for describing an operation example of the imaging apparatus 10 in the acquisition of a fingerprint pattern. FIG. 5 shows an example in which, in a state where the finger S is mounted on the mounting region 1001a, first irradiation lights IL1 are radiated from first light sources 111, and scattered light SL11 that is obtained by the first irradiation lights IL1 being scattered at the contact interface between the finger S and the first light guide plate 101 is injected into the imaging unit 120. Further, the imaging apparatus 10 shown in FIG. 5 is the same as the configuration of the imaging apparatus 10 shown in FIG. 2.

Note that the wavelength of the first irradiation light IL1 is preferably a wavelength included in the wavelength band of visible light, as described above.

The first irradiation lights IL1 are first radiated from the first light sources 111 provided on edge portions of the first light guide plates 101, and propagate through the interior of the first light guide plate 101 while reflecting at the upper surface and the lower surface of the first light guide plate 101. Then, when the first irradiation lights IL1 arrive at a position in the contact interface between the mounting region 1001a and the finger S corresponding to a ridge of the fingerprint, the first irradiation lights IL1 are scattered at this position, and scattered light SL11 can be generated.

Figure 6:
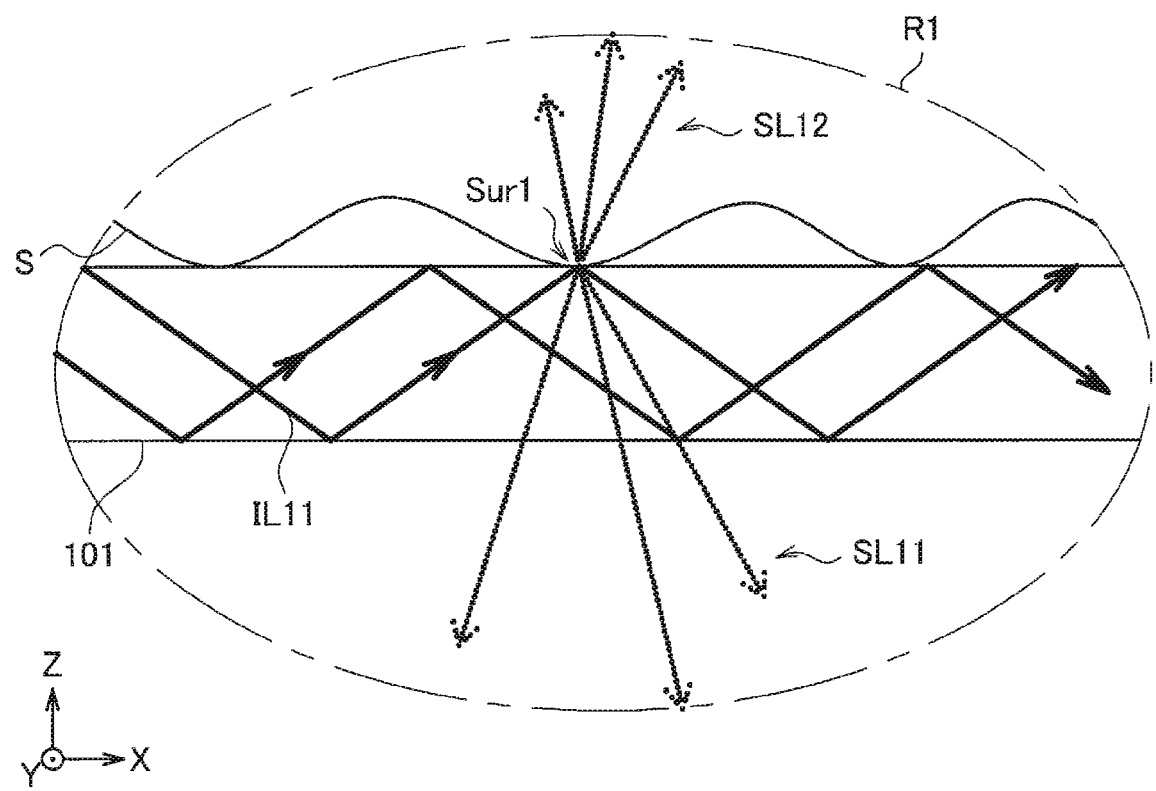
FIG. 6 is a diagram for describing generation of scattered light.

The generation of scattered light SL11 will now be described with reference to FIG. 6. FIG. 6 is a diagram for describing the generation of scattered light SL11. The region shown by alternate long and short dash line R1 of FIG. 6 corresponds to the region shown by alternate long and short dash line R1 of FIG. 5.

If the region shown by alternate long and short dash line R1 is enlarged as shown in FIG. 6, the surface of the finger S has a concave-convex shape due to ridges and valleys of the fingerprint. Portions of the concave-convex shape corresponding to ridges of the fingerprint are in contact with the mounting region 1001a of the first light guide plate 101.

Here, it is assumed that a first irradiation light IL11 is incident on a contact interface Sur1 between a ridge of the fingerprint of the finger S and the mounting region 1001a. Thus, the first irradiation light IL11 is scattered at the contact interface Sur1, and scattered lights SL11 and SL12 are generated. The scattered light SL11 is scattered toward the imaging unit 120, and the scattered light SL12 is scattered toward the interior of the finger S. Part of the scattered light SL11 is injected into the imaging unit 120. The imaging unit 120 images the injected scattered light SL11, and generates a captured image. The positions of light receiving elements of the imaging unit 120 that receive scattered lights SL11 correspond to the positions of ridges of the fingerprint, and therefore the generated captured image includes a fingerprint pattern of the finger S.

Note that, in the present operation example, also a captured image that includes not only a fingerprint pattern of the finger S but also the surface structure or the surface state of the finger S (for example, the state of the skin) can be acquired. Further, the timing of imaging of scattered light SL11 by the imaging unit 120 may be synchronized with the radiation timing of the first light source 111.

Acquisition of Vein Pattern

Figure 7:
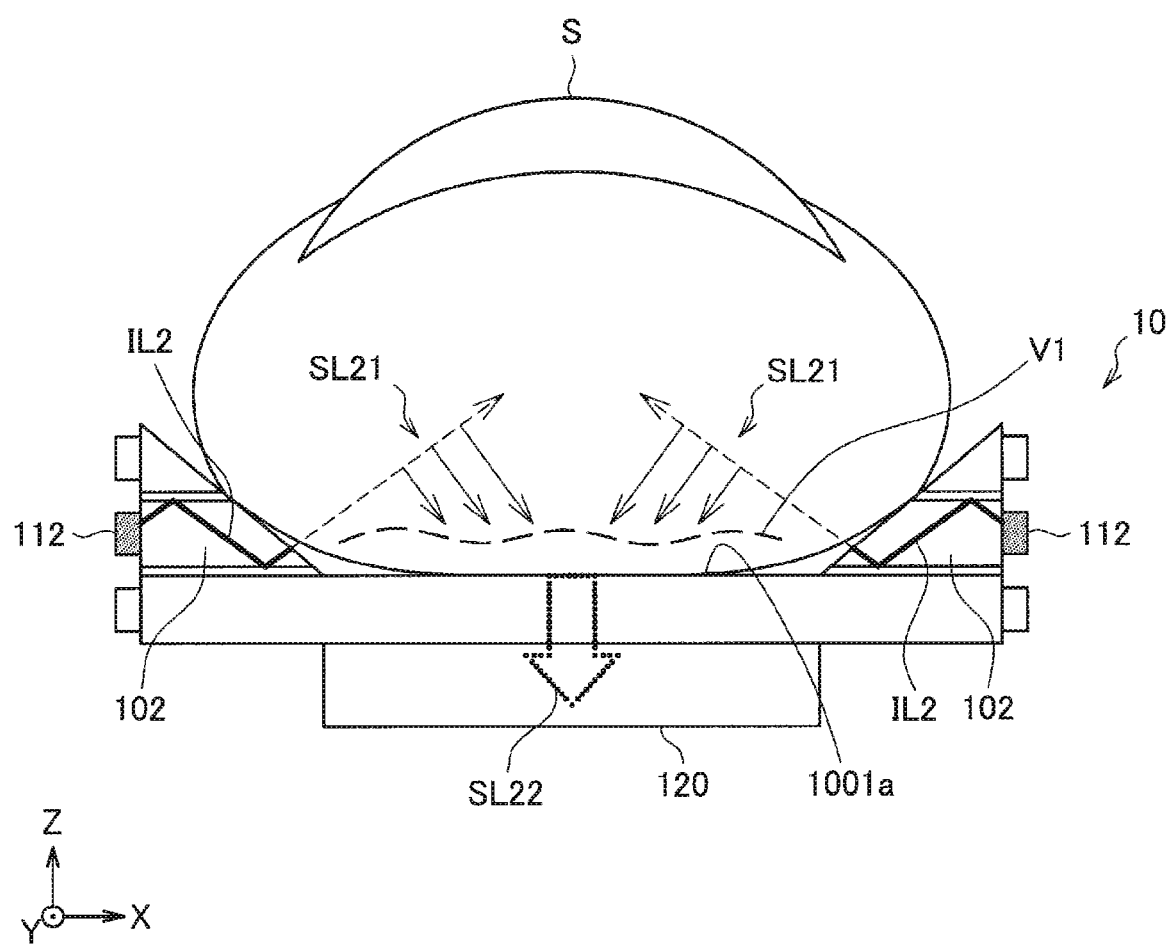
FIG. 7 is a diagram for describing a first operation example of the imaging apparatus in acquisition of a vein pattern.

FIG. 7 is a diagram for describing a first operation example of the imaging apparatus 10 in the acquisition of a vein pattern. FIG. 7 shows an example in which, in a state where the finger S is mounted on the mounting region 1001a, second irradiation lights IL2 are radiated from second light sources 112, and the second irradiation lights IL2 are injected into the interior of the finger S. Further, the imaging apparatus 10 shown in FIG. 7 is the same as the configuration of the imaging apparatus 10 shown in FIG. 2.

Note that the wavelength of the second irradiation light IL2 is preferably a wavelength of near-infrared light having high transmissivity to bodily tissues, as described above.

A living body is a good scatterer of near-infrared light; therefore, the second irradiation lights IL2 injected in the interior of the finger S propagate while scattering in various directions in the interior of the finger S. Part of these scattered lights travel through the vein layer described above from its back surface toward the surface of the finger, as scattered lights SL21, and are transmitted through veins V on the way. Part of the scattered light SL22 that has been transmitted through the veins V is injected into the imaging unit 120.

The imaging unit 120 images the injected scattered light SL22, and generates a captured image. The generated captured image includes shadows that can occur due to part of the scattered lights SL21 being absorbed in the veins V. The shadows correspond to a vein pattern related to the veins V1 of the finger S, as described above.

Note that the captured image obtained by imaging scattered light SL22 generated on the basis of the second irradiation light IL2 may include not only a vein pattern but also an image derived from other living body structures etc. related to the finger S. This is because, when the scattered light SL22 that has been transmitted through the veins V1 is being transmitted through the surface of the finger S, the scattered light SL22 is further absorbed or scattered by the fingerprint etc. The removal or the like of such an image can be performed by, although details are described later, performing image processing using a captured image obtained by imaging scattered light SL11 generated on the basis of the first irradiation light ILL Note that, in the present operation example, also a captured image that includes not only a vein pattern of the finger S but also the interior structure or the interior state of the finger S (for example, a pulse wave of arteries of the finger S, etc.) can be acquired. Further, the timing of imaging of scattered light SL22 by the imaging unit 120 may be synchronized with the radiation timing of the second light source 112.

Another Operation Example in Acquisition of Vein Pattern

Figure 8:
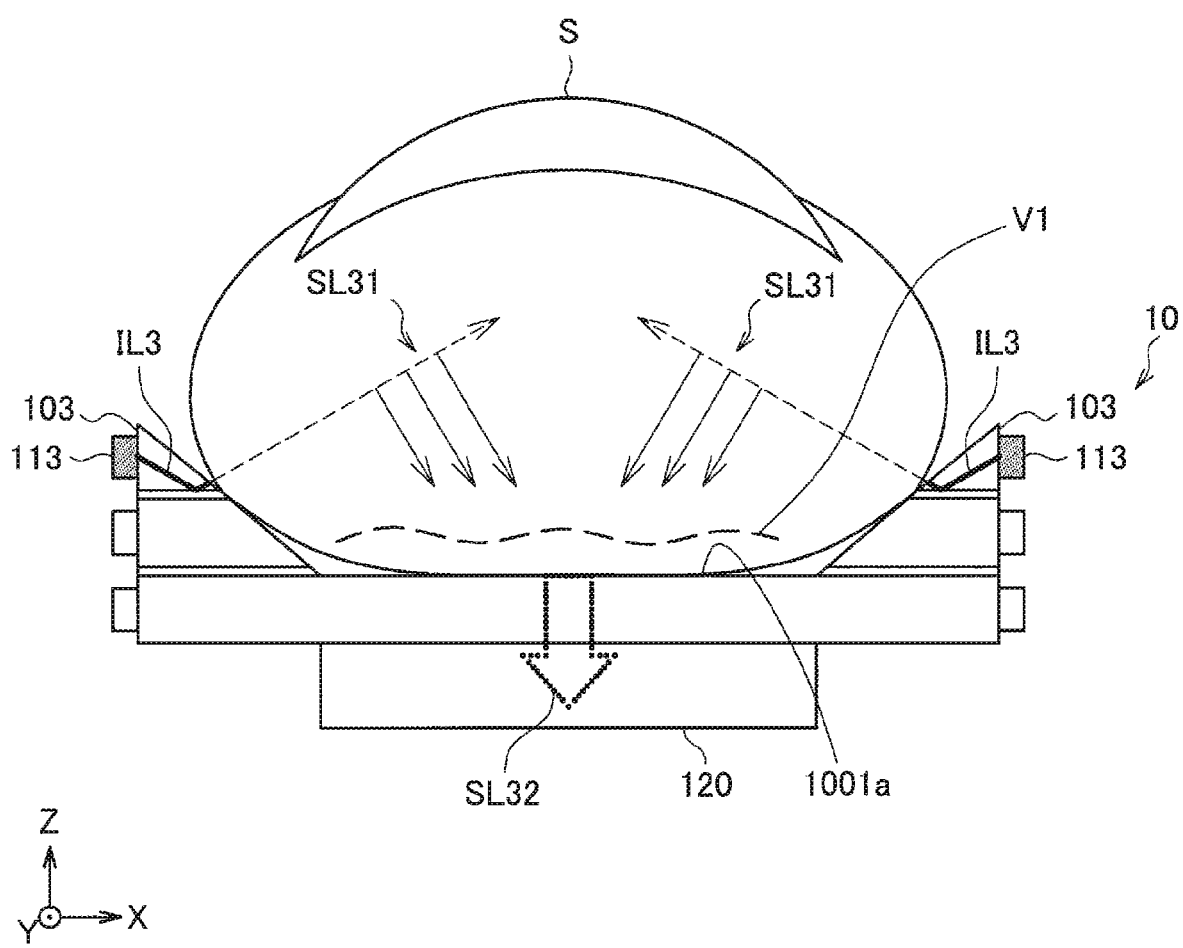
FIG. 8 is a diagram for describing a second operation example of the imaging apparatus in acquisition of a vein pattern.

Note that the imaging of the acquisition of a vein pattern described above may be performed using the third irradiation light IL3 applied from the third light source 113. FIG. 8 is a diagram for describing a second operation example of the imaging apparatus 10 in the acquisition of a vein pattern. FIG. 8 shows an example in which, in a state where the finger S is mounted on the mounting region 1001a, third irradiation lights IL3 are radiated from third light sources 113, and the third irradiation lights IL3 are injected into the interior of the finger S. Note that the imaging apparatus 10 shown in FIG. 8 is the same as the configuration of the imaging apparatus 10 shown in FIG. 2. Further, the wavelength of the third irradiation light IL3 is preferably a wavelength of near-infrared light having high transmissivity to bodily tissues, as described above.

The third irradiation lights IL3 injected in the interior of the finger S propagate while scattering in various directions in the interior of the finger S. Part of these scattered lights travel through the vein layer described above from its back surface toward the surface of the finger, as scattered lights SL31, and are transmitted through veins V on the way. The scattered light SL32 that has been transmitted through the veins V is injected into the imaging unit 120. Thereby, a captured image including a vein pattern can be obtained similarly to the example described above.

Hereinabove, operation examples of the imaging apparatus 10 in the acquisition of a fingerprint pattern and a vein pattern are described. By the imaging apparatus 10, a captured image including a fingerprint pattern (the first captured image) can be obtained on the basis of the first irradiation light, and a captured image including a vein pattern (the second captured image) can be obtained on the basis of the second irradiation light (or the third irradiation light). Thereby, living body information used for fingerprint authentication and vein authentication in the information processing apparatus 20 in a later stage (that is, a fingerprint pattern and a vein pattern) can be acquired by one imaging apparatus 10.

The size in the thickness direction (Z-axis direction) (thickness) of the imaging apparatus 10 depends on at least the thicknesses of the first light guide plate 101, the second light guide plate 102, and the imaging unit 120. The first light source 111 and the second light source 112 used to obtain a fingerprint pattern and a vein pattern are provided on edge portions of the respective light guide plates, and therefore do not influence the thickness of the imaging apparatus 10. Hence, the thickness of the imaging apparatus 10 can be made as small as possible. Thereby, the convenience of the authentication processing apparatus 1 is improved.

Note that, although in the operation examples described above it is assumed that the first irradiation light is visible light and the second irradiation light (and the third irradiation light) is near-infrared light, the wavelength of each irradiation light is not limited to this example. The wavelength of each irradiation light may be selected in accordance with the imaging object, such as a fingerprint or veins, as appropriate. Further, it is preferable that the wavelength of the first irradiation light and the wavelength of the second irradiation light (and the third irradiation light) be different. By varying the wavelength of irradiation light, a difference can be obtained between irradiation lights in the degree of absorption or scattering at a living body structure and a living body component. Hence, the difference between a captured image obtained on the basis of the first irradiation light and a captured image obtained on the basis of the second irradiation light can be made more distinctive. That is, the accuracy of biometric authentication using these captured images can be enhanced more. Further, by varying the wavelength, captured images including patterns based on different living body structures or living body components can be acquired. Thereby, the number of variations of patterns used for biometric authentication is increased. That is, more secure biometric authentication can be performed.

Further, as shown in FIG. 8, in the imaging apparatus 10, a captured image including a vein pattern or the like may be generated using the third irradiation light that is applied from the third light source 113 and propagates through the interior of the third light guide plate 103. Thereby, irradiation light can be injected into a part of a living body, such as a finger, from different heights. Thus, for example, a vein pattern in which not only a vein layer existing near the outer layer of the finger but also a vein layer existing near the center or the like of the finger is caused to be reflected can be acquired.

Note that, although in the examples shown in FIG. 7 and FIG. 8 the second irradiation light and the third irradiation light are each radiated singly from the respective light sources, the second irradiation light and the third irradiation light may be injected into the finger simultaneously. Thereby, the intensity of scattered light from the finger can be increased. Thus, the captured image including a vein pattern can be more vivid.

Hereinabove, operation examples of the imaging apparatus 10 in the acquisition of a fingerprint pattern and a vein pattern are described; however, the imaging apparatus 10 according to the present embodiment is not limited to being used for the acquisition of captured images including the patterns described above. For example, the imaging apparatus 10 according to the present embodiment may be used for the acquisition of a captured image regarding each of the objects to be imaged shown in Table 1 above. More specifically, a captured image for analyzing the surface structure or the surface state of a living body, such as a characteristic or a state such as the clearness of the skin (the cuticle) of the finger S, may be acquired by the first irradiation light radiated from the first light source 111. Further, a captured image for analyzing the interior structure or the interior state of a living body, such as the pulsation of the finger S, may be acquired by the second irradiation light radiated from the second light source 112. Note that processing related to these pieces of biometric authentication and analysis is described later.

Modification Examples

Figure 9:
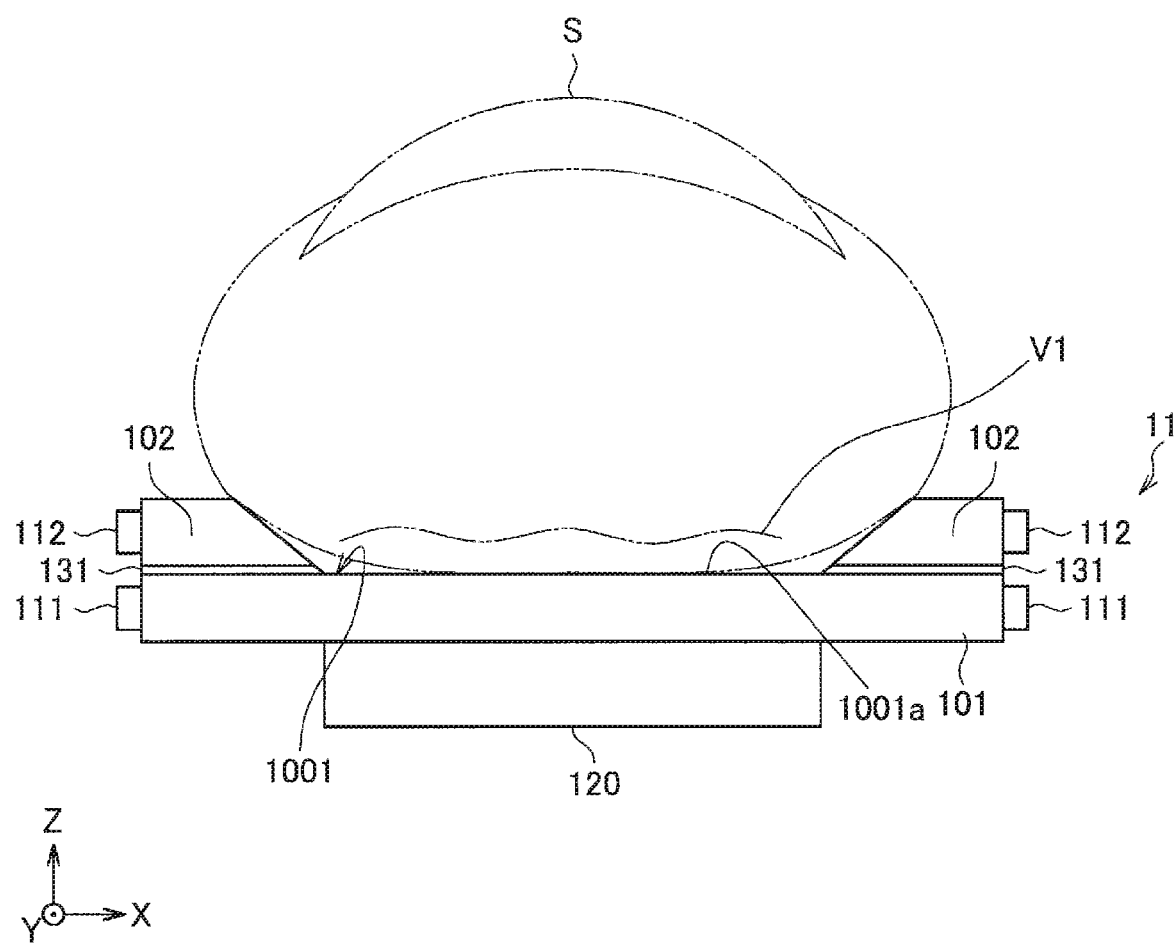
FIG. 9 is a diagram showing a configuration of a modification example of an imaging apparatus according to the embodiment.

Although the imaging apparatus 10 according to the present embodiment has a structure in which three light guide plates are stacked as shown in FIG. 2 and FIG. 3, the present technology is not limited to this example. FIG. 9 is a diagram showing the configuration of a modification example of an imaging apparatus 11 according to the present embodiment.

As shown in FIG. 9, the imaging apparatus 11 according to the present modification example mainly includes the first light guide plate 101, the second light guide plates 102, the first light sources 111, the second light sources 112 (112a to 112c), and the imaging unit 120. Further, the first light blocking body 131 is provided so as to be sandwiched between the first light guide plate 101 and the second light guide plate 102.

In this configuration, in a case where a finger S is mounted on the mounting region 1001a, a captured image related to the surface structure or the surface nature of the finger S (a fingerprint or the like) can be acquired by imaging scattered light resulting from the first irradiation light. Furthermore, a captured image related to the interior structure or the interior state of the finger S (veins or the like) can be acquired by imaging scattered light resulting from the second irradiation light.

Further, a plurality of light guide plates including the third light guide plate 103 may be further stacked on the upper side of the second light guide plate 102. In this case, a light source that applies irradiation light to the interior of a stacked light guide plate may be further provided on an edge portion of the stacked light guide plate. By forming a structure in which a light guide plate is further caused to be stacked, even in a case where the thickness of a part of a living body, such as the finger S, is increased, irradiation light can be injected into the interior of the living body more reliably. Therefore, a captured image in which the interior of a living body is caused to be reflected can be generated more reliably.

Further, in the imaging apparatus 10 according to the present embodiment, a sensor for identifying whether a finger S is mounted on the mounting region 1001a of the first light guide plate 101 or not may be further provided. Thereby, the radiation of irradiation light from each light source and operation related to imaging by the imaging unit 120 can be performed after it is identified that a finger S is mounted. The sensor may include any sensor, such as a pressure sensor, an optical sensor, an electrostatic capacitance sensor, or an ultrasonic sensor. Further, the imaging element provided in the imaging unit 120 may serve as the sensor.

Hereinabove, the imaging apparatus 10 according to the present embodiment is described.

1.3. Information Processing Apparatus

Returning to FIG. 1 again, the information processing apparatus 20 according to the present embodiment is described.

Configuration Example

As shown in FIG. 1, the information processing apparatus 20 according to the present embodiment includes an imaging control unit 210, a data acquisition unit 220, a processing unit 230, an output control unit 240, and a memory unit 250.

Imaging Control Unit

The imaging control unit 210 includes, for example, a central processing unit (CPU), a read-only memory (ROM), a random access memory (RAM), etc. The imaging control unit 210 performs driving control related to the imaging apparatus 10, and supervises processing related to imaging by the imaging apparatus 10. For example, the imaging control unit 210 controls the radiation timing of irradiation light, the intensity of irradiation light, etc. in each light source. Further, the imaging control unit 210 performs control related to imaging such as the imaging timing, the exposure time, and the aperture in the imaging unit 120. The imaging control unit 210 controls the imaging apparatus 10 via a communication device included in the information processing apparatus 20.

By the imaging control unit 210 performing control like the above, each light source can radiate an irradiation light with a prescribed wavelength and a prescribed intensity at an appropriate timing, and a captured image in accordance with the radiation timing of each light source can be generated. Such a radiation timing and such an imaging timing may be determined on the basis of, for example, a signal acquired from the sensor described above or a signal coming from a terminal or the like in which the imaging apparatus 10 is provided.

Data (captured image data) related to a captured image generated by the imaging apparatus 10 controlled by the imaging control unit 210 are acquired by the data acquisition unit 220 described later. Note that the captured image data may include not only the data of the captured image itself but also the time instant of generation of the captured image and the content of control by the imaging control unit 210.

Further, when performing the control of the imaging apparatus 10, the imaging control unit 210 may refer to various programs, parameters, databases, etc. recorded in the memory unit 250 described later, as appropriate. For example, the imaging control unit 210 may refer to a program, etc. related to imaging corresponding to processing that is performed by the processing unit 230 described later, as appropriate.

Data Acquisition Unit

The data acquisition unit 220 includes, for example, a CPU, a ROM, a RAM, etc. The data acquisition unit 220 acquires captured image data generated by the imaging apparatus 10 via the communication device mentioned above.

The data acquisition unit 220 outputs the acquired captured image data to the processing unit 230. Further, the data acquisition unit 220 may record the acquired captured image data in the memory unit 250.

Processing Unit

The processing unit 230 includes, for example, a CPU, a ROM, a RAM, etc. On the basis of a captured image generated by the imaging apparatus 10, the processing unit 230 performs processing regarding a part of a living body (for example, a finger) that has been the imaging object.

The processing regarding a part of a living body by the processing unit 230 includes biometric authentication processing, for example. More specifically, the processing unit 230 acquires a captured image including a fingerprint pattern (the first captured image) and a captured image including a vein pattern (the second captured image), determines the fingerprint pattern and the vein pattern by image analysis, and performs authentication processing regarding the determined patterns.

The configuration of the processing unit 230 for performing processing including such biometric authentication processing is described later.

Note that, although the processing unit 230 according to the present embodiment performs biometric authentication processing by using a captured image generated by the imaging apparatus 10, the processing by the processing unit 230 is not limited to this example. For example, the processing unit 230 may perform analysis processing regarding the structure or state of the surface or interior of a living body. Also details of the analysis processing are described later.

A result of processing by the processing unit 230 is outputted to the output control unit 240. Further, the processing unit 230 may record a processing result in the memory unit 250. Further, when performing various pieces of processing, the processing unit 230 may refer to various programs, parameters, databases, etc. recorded in the memory unit 250, as appropriate. For example, in order to collate a fingerprint pattern and a vein pattern that are determined by image analysis from acquired captured images, the image processing unit 230 may refer to a database including templates of a fingerprint pattern, a vein pattern, etc. that is stored in the memory unit 250, as appropriate.

Output Control Unit

The output control unit 240 includes, for example, a CPU, a ROM, a RAM, etc. The output control unit 240 performs control regarding the output of information related to a processing result acquired from the processing unit 230.

For example, the output control unit 240 may perform control that causes information related to a processing result to be displayed on a not-illustrated display device such as a display or a touch panel. More specifically, the output control unit 240 may cause information related to a result of biometric authentication processing by the processing unit 230 to be displayed on a display or the like of a terminal in which the authentication processing apparatus 1 is provided.

Further, the output control unit 240 may output information related to a processing result to a terminal or a device that performs processing utilizing a result of biometric authentication. Thereby, the terminal or device can perform various pieces of processing on the basis of the outputted information.

Note that the terminal or device described above that performs processing utilizing a result of biometric authentication is not necessarily limited to a terminal or a device in which the authentication processing apparatus 1 (or the imaging apparatus 10) is provided, and may be a terminal or a device in which the authentication processing apparatus 1 (or the imaging apparatus 10) is not provided. In this case, information related to a processing result may be transmitted to the terminal or device mentioned above via a communication device or the like included in the information processing apparatus 20. For example, in a case where the authentication processing apparatus 1 is provided in a mobile terminal, a room entry and exit management device that performs unlocking or locking processing on the basis of a result of biometric authentication processing can perform the unlocking or locking processing mentioned above by receiving, from the mobile terminal, a result of biometric authentication processing obtained by the authentication processing apparatus 1.

Note that, when performing various pieces of output control, the output control unit 240 may refer to various programs, parameters, databases, etc. recorded in the memory unit 250, as appropriate.

Memory Unit

The memory unit 250 includes a RAM, a storage device, or the like provided in the information processing apparatus 20 according to the present embodiment. In the memory unit 250, data used for various pieces of processing in the function units of the information processing apparatus 20, etc. are stored. For example, in the memory unit 250, data of templates of various patterns such as a fingerprint pattern and a vein pattern to be used for biometric authentication are stored. Further, the memory unit 250 may store data related to captured images acquired by the data acquisition unit 220 or the like, data related to results of processing by the processing unit 230, etc. Furthermore, as well as these data, various parameters, reports on processing still in progress, etc. that are required to be saved when the information processing apparatus 20 performs some kind of processing, various databases, etc. may be stored, as appropriate. The imaging control unit 210, the data acquisition unit 220, the processing unit 230, and the output control unit 240 can freely perform reading and writing on the memory unit 250.

Configuration Example of Processing Unit

Figure 10:
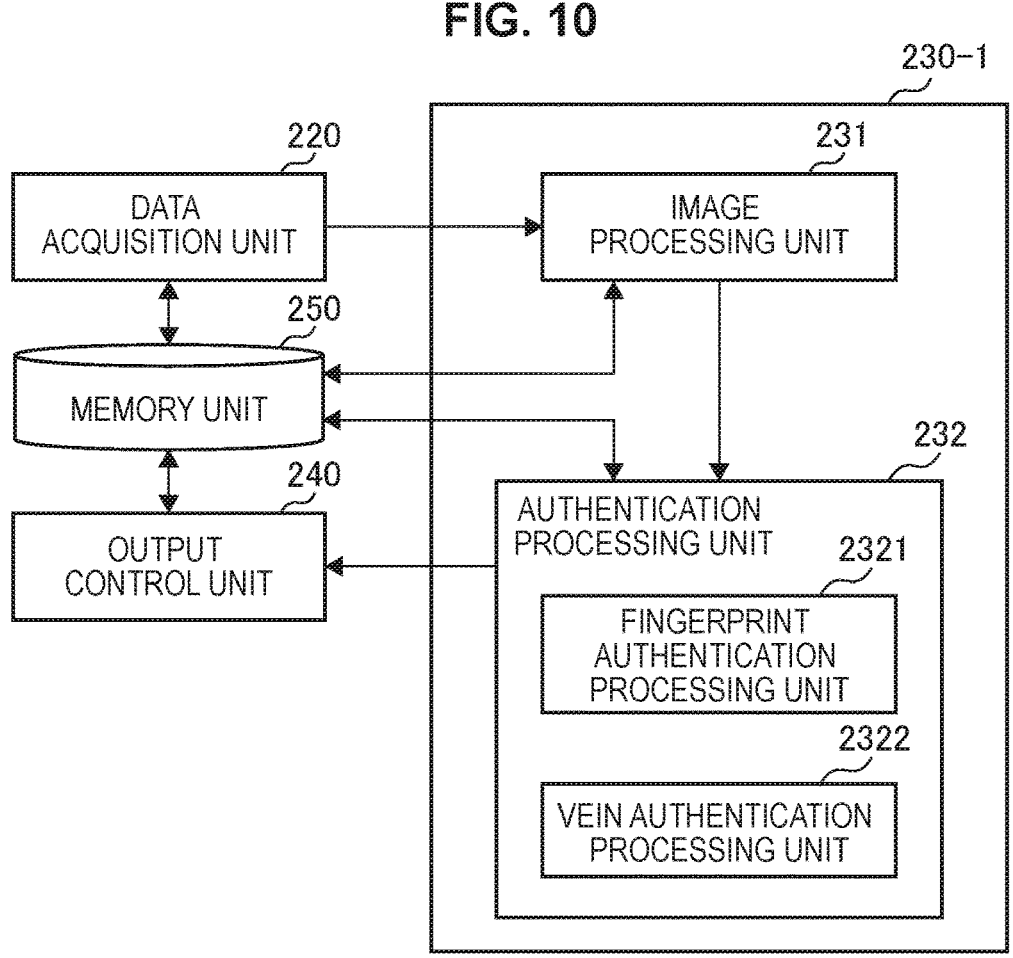
FIG. 10 is a block diagram showing a configuration example of a processing unit according to the embodiment.

Next, a configuration example of the processing unit 230 (230-1) according to the present embodiment is described with reference to FIG. 10. FIG. 10 is a block diagram showing a configuration example of the processing unit 230-1 according to the present embodiment.

As shown in FIG. 10, the processing unit 230-1 according to the present embodiment includes an image processing unit 231 and an authentication processing unit 232. Furthermore, the authentication processing unit 232 mainly includes a fingerprint authentication processing unit 2321 and a vein authentication processing unit 2322.

Image Processing Unit

The image processing unit 231 performs image processing on captured images acquired from the data acquisition unit 220, and extracts various patterns such as a fingerprint pattern and a vein pattern. For example, the image processing unit 231 may perform accentuation, denoising, etc. on captured images by using various filters, algorithms, etc. Thereby, various patterns included in the captured images are extracted more clearly.

Known filters related to smoothing and denoising, such as a moving average filter, a differential filter, a median filter, and a Gaussian filter, may be used in image processing by the image processing unit 231, for example. Further, known algorithms related to binarization and thinning may be used in the image processing mentioned above. Further, the filter or algorithm used for image processing may be selected in accordance with the object to be extracted, as appropriate.

The image processing unit 231 outputs image data including various patterns extracted by image processing to the authentication processing unit 232. Further, the image data may be recorded in the memory unit 250.

Authentication Processing Unit

On the basis of various patterns included in image data outputted from the image processing unit 231 and various templates registered in advance, the authentication processing unit 232 performs the authentication of the various patterns included in the image data.

The authentication processing unit 232 according to the present embodiment includes the fingerprint authentication processing unit 2321 that performs the authentication of a fingerprint pattern and the vein authentication processing unit 2322 that performs the authentication of a vein pattern.

Fingerprint Authentication Processing Unit

On the basis of a fingerprint pattern included in image data outputted from the image processing unit 231 and a template of a fingerprint pattern (a fingerprint template) recorded in the memory unit 250 or the like in advance, the fingerprint authentication processing unit 2321 performs the authentication of the fingerprint pattern included in the image data. The image data herein refer to image data obtained by image processing by the image processing unit 231 on a captured image (the first captured image) that is generated by the imaging apparatus 10 when the first irradiation light is applied.

The fingerprint authentication processing unit 2321 may perform the authentication of a fingerprint pattern by known technology. For example, the fingerprint authentication processing unit 2321 may collate a fingerprint pattern with a fingerprint template on the basis of the shape of the fingerprint pattern. More specifically, the fingerprint authentication processing unit 2321 may extract feature points based on endpoints or bifurcations of ridges of a fingerprint called minutiae in regard to a fingerprint pattern, and may perform matching processing of a fingerprint template on the basis of information related to the feature points. Further, the fingerprint authentication processing unit 2321 may further perform matching processing in accordance with the number of ridges passing between ones of the feature points mentioned above, etc. Further, the fingerprint authentication processing unit 2321 may perform pattern matching processing in regard to a fingerprint pattern. If a fingerprint template that agrees with the fingerprint pattern or resembles the fingerprint pattern by more than or equal to a prescribed standard is found, the fingerprint authentication processing unit 2321 authenticates the fingerprint pattern. On the other hand, if a fingerprint template resembling the fingerprint pattern by more than or equal to the prescribed standard is not found, the fingerprint pattern is not authenticated.

Vein Authentication Processing Unit

On the basis of a vein pattern included in image data outputted from the image processing unit 231 and a template of a vein pattern (a vein template) recorded in the memory unit 250 or the like in advance, the vein authentication processing unit 2322 performs the authentication of the vein pattern included in the image data. The image data herein refer to image data obtained by image processing by the image processing unit 231 on a captured image (the second captured image) that is generated by the imaging apparatus 10 when the second irradiation light is applied.

The vein authentication processing unit 2322 may perform the authentication of a vein pattern by known technology. For example, the vein authentication processing unit 2322 may collate a vein pattern with a vein template on the basis of the shape of the vein pattern. More specifically, the vein authentication processing unit 2322 may extract feature points based on endpoints or bifurcations of blood vessels in a vein pattern, and may perform matching processing of a vein template on the basis of information related to the feature points. Further, the vein authentication processing unit 2322 may further perform matching processing in accordance with the number of ridges passing between ones of the feature points mentioned above, etc. Further, the vein authentication processing unit 2322 may perform pattern matching processing in regard to a vein pattern. If a vein template that agrees with the vein pattern or resembles the vein pattern by more than or equal to a prescribed standard is found, the vein authentication processing unit 2322 authenticates the vein pattern. On the other hand, if a vein template resembling the vein pattern by more than or equal to the prescribed standard is not found, the vein pattern is not authenticated.

The authentication processing unit 232 performs authentication processing in regard to at least one of various patterns such as a fingerprint pattern and a vein pattern, and outputs the authentication result to the output control unit 240, the memory unit 250, etc. The authentication result herein includes, for example, the presence or absence of a template that has matched a pattern, data of personal information etc. associated with a template that has matched, etc. Further, the authentication processing unit 232 may associate the authentication result mentioned above with the time instant when the authentication processing is performed, etc., and may output the data as an authentication history to the output control unit 240, the memory unit 250, etc. Thereby, who when performed authentication processing or used the imaging apparatus 10 can be found.

Further, the authentication processing unit 232 may output a plurality of authentication results (for example, an authentication result of a fingerprint pattern and an authentication result of a vein pattern) while associating them together. Thereby, biometric authentication by what is called multimodal authentication can be performed, and the accuracy of biometric authentication can be further improved. In the multimodal authentication, for example, the assessment that the authentication of a user has succeeded may be made in a case of having succeeded in the authentication of a fingerprint pattern and furthermore having succeeded in the authentication of a vein pattern. On the other hand, the assessment that the authentication of a user has succeeded may be made also in a case of having succeeded in at least one of the authentication of a fingerprint pattern and the authentication of a vein pattern. The assessment criterion in assessment processing using such multimodal authentication may be set in accordance with various pieces of processing to which biometric authentication is caused to be applied, as appropriate.

Supplements

Note that the templates of various patterns described above may be registered in the memory unit 250 or the like while being associated with personal information, as described above. Further, the templates of various patterns may be associated with each other. For example, a fingerprint template and a vein template related to one user may be associated with each other. Thereby, more secure authentication can be performed.

Further, templates to be collated in the authentication of various patterns may not necessarily be recorded in the memory unit 250. For example, the templates may be stored in a server, a cloud, etc. in the outside. In this case, the processing unit 230-1 (the authentication processing unit 232) may acquire the templates mentioned above by, in authentication processing, accessing a server or a cloud via a communication device, as appropriate.

Further, the authentication processing unit 232 mentioned above may perform not only authentication processing of various patterns such as a fingerprint pattern and a vein pattern included in acquired image data, but also the processing of registering various patterns. For example, the authentication processing unit 232 may register, in the memory unit 250, a fingerprint pattern or a vein pattern included in image data after subjected to image processing by the image processing unit 231, as a template. Further, at the time of registration in the memory unit 250, the authentication processing unit 232 may register personal information etc. of a user while associating them with a template. The registered template may have header information according to a standard such as a Common Biometric Exchange File Format (CBEFF) framework, for example.

1.4. Flows of Processing

Figure 11:
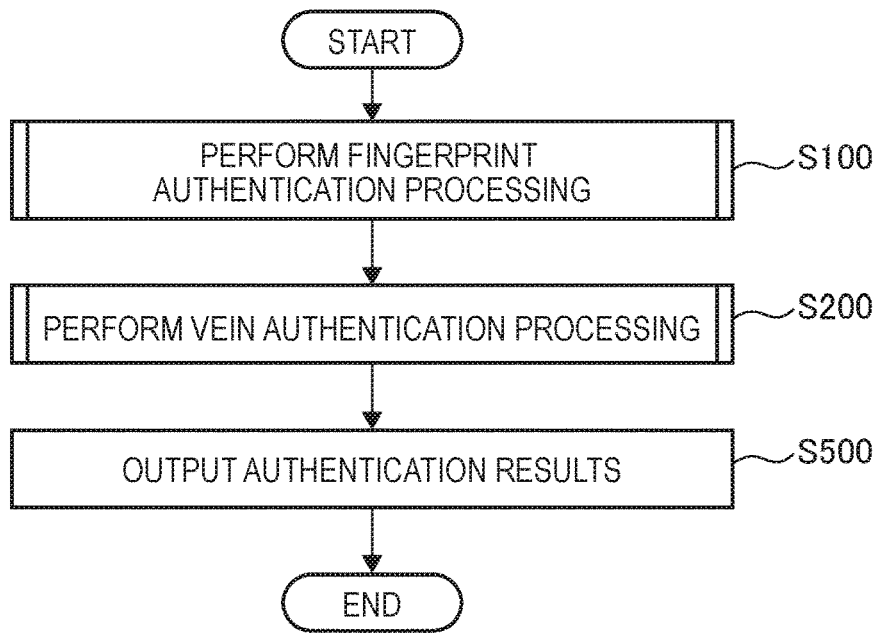
FIG. 11 is a flow chart showing an example of a flow of processing by the authentication processing apparatus according to the embodiment.

Next, examples of flows of processing by the authentication processing apparatus 1 according to the present embodiment are described. FIG. 11 is a flow chart showing an example of a flow of processing by the authentication processing apparatus 1 according to the present embodiment. As shown in the flow chart shown in FIG. 11, the authentication processing apparatus 1 performs fingerprint authentication processing (step S100) and vein authentication processing (step S200), for example. Note that the order of fingerprint authentication processing and vein authentication processing is not limited to the order according to the flow chart shown in FIG. 11. Hereinbelow, examples of flows of processing in fingerprint authentication processing and vein authentication processing by the authentication processing apparatus 1 according to the present embodiment are described.

Fingerprint Authentication Processing

Figure 12:
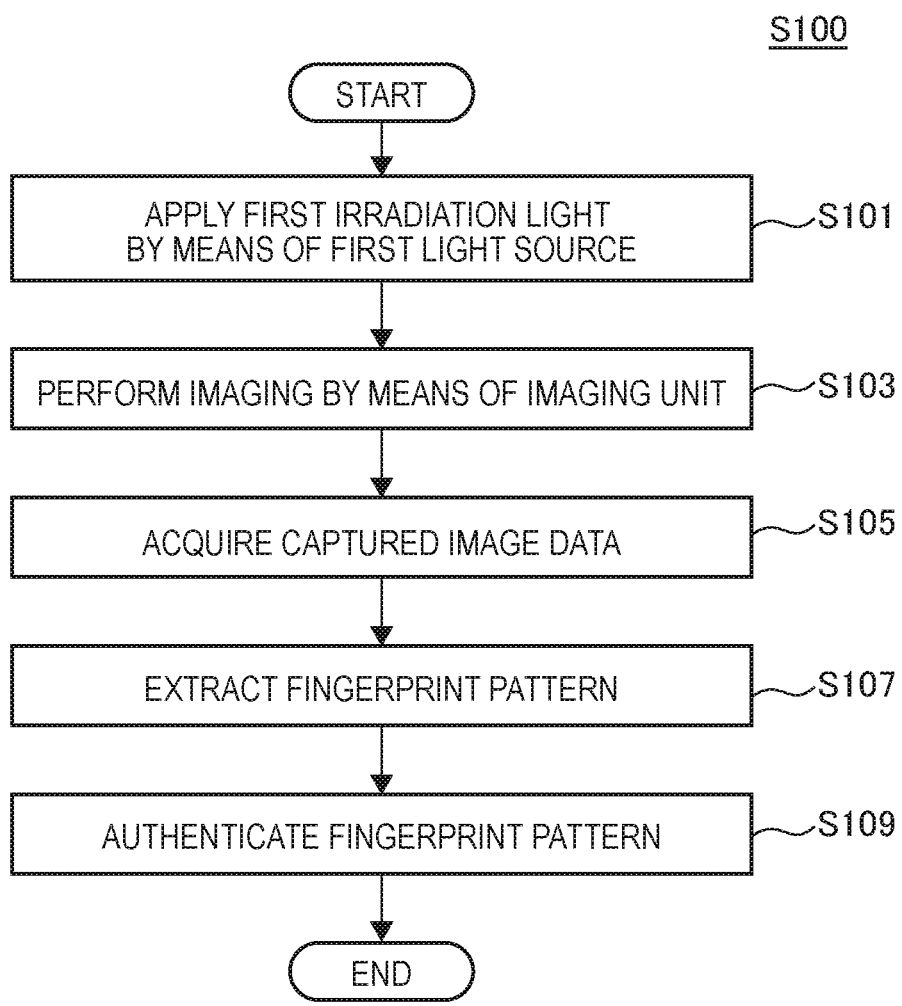
FIG. 12 is a flow chart showing an example of a flow of fingerprint authentication processing by the authentication processing apparatus according to the embodiment.

FIG. 12 is a flow chart showing an example of a flow of fingerprint authentication processing by the authentication processing apparatus 1 according to the present embodiment. Referring to FIG. 12, first, by the control of the imaging control unit 210, the authentication processing apparatus 1 radiates a first irradiation light from the first light source 111, and applies the first irradiation light to the interior of the first light guide plate 101 (step S101). Thereby, the first irradiation light is scattered at the contact interfaces between ridges of a fingerprint of a finger mounted on the mounting region 1001a of the first light guide plate 101 and the first light guide plate 101, and part of the scattered light is injected into the imaging unit 120. Note that the first irradiation light preferably has a wavelength corresponding to green light.

Next, the authentication processing apparatus 1 uses the imaging unit 120 to image the injected scattered light (step S103). Then, the authentication processing apparatus 1 uses the data acquisition unit 220 to acquire generated captured image data (step S105).

Next, the authentication processing apparatus 1 uses the processing unit 230-1 to extract a fingerprint pattern from the acquired captured image data (step S107). Specifically, the image processing unit 231 performs various pieces of image processing on the acquired captured image data, and extracts a fingerprint pattern included in the captured image.

Next, the authentication processing apparatus 1 uses the processing unit 230-1 to perform the authentication of the fingerprint pattern (step S109). Specifically, the authentication processing unit 232 (the fingerprint authentication processing unit 2321) collates the extracted fingerprint pattern with a fingerprint template; if a fingerprint template that agrees with the fingerprint pattern or resembles the fingerprint pattern by more than or equal to a prescribed standard is found, the authentication processing unit 232 authenticates the fingerprint pattern. On the other hand, if a fingerprint template resembling the fingerprint pattern by more than or equal to the prescribed standard is not found, the fingerprint pattern is not authenticated.

Vein Authentication Processing

Figure 13:
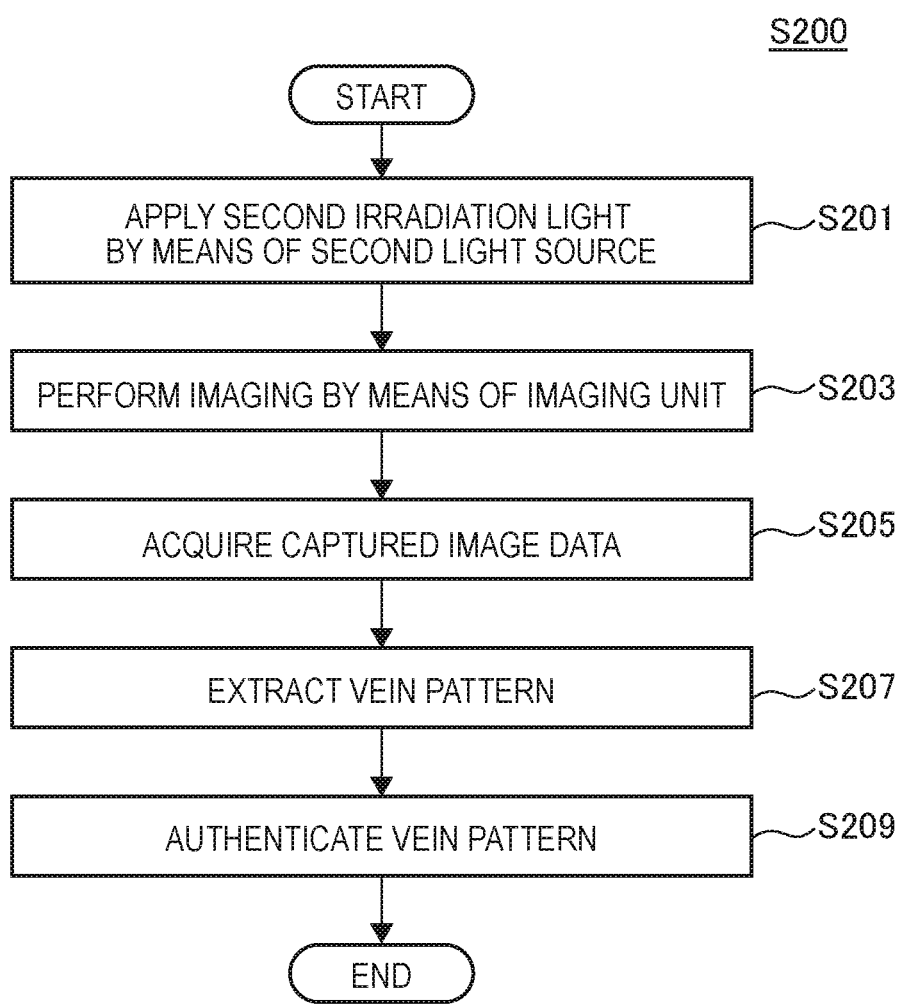
FIG. 13 is a flow chart showing an example of a flow of vein authentication processing by the authentication processing apparatus according to the embodiment.

FIG. 13 is a flow chart showing an example of a flow of vein authentication processing by the authentication processing apparatus 1 according to the present embodiment. Referring to FIG. 13, first, by the control of the imaging control unit 210, the authentication processing apparatus 1 radiates a second irradiation light from the second light source 112, and applies the second irradiation light to the interior of the second light guide plate 102 (step S201). Thereby, the second irradiation light emitted from a side surface of the second light guide plate 102 on the mounting region 1001a side is applied to a finger, the second irradiation light is scattered in the interior of the finger, and part of the scattered light is injected into the imaging unit 120. Note that the second irradiation light preferably has a wavelength corresponding to near-infrared light.

Next, the authentication processing apparatus 1 uses the imaging unit 120 to image the injected scattered light (step S203). Then, the authentication processing apparatus 1 uses the data acquisition unit 220 to acquire generated captured image data (step S205).

Next, the authentication processing apparatus 1 uses the processing unit 230-1 to extract a vein pattern from the acquired captured image data (step S207). Specifically, the image processing unit 231 performs various pieces of image processing on the acquired captured image data, and extracts a vein pattern included in the captured image.

Next, the authentication processing apparatus 1 uses the processing unit 230-1 to perform the authentication of the vein pattern (step S209). Specifically, the authentication processing unit 232 (the vein authentication processing unit 2322) collates the extracted vein pattern with a vein template; if a vein template that agrees with the vein pattern or resembles the vein pattern by more than or equal to a prescribed standard is found, the authentication processing unit 232 authenticates the vein pattern. On the other hand, if a vein template resembling the vein pattern by more than or equal to the prescribed standard is not found, the vein pattern is not authenticated.

Referring to FIG. 11 again, the authentication processing apparatus 1 uses the output control unit 240 to output the authentication results in fingerprint authentication processing and vein authentication processing (step S500).

Hereinabove, examples of flows of processing by the authentication processing apparatus 1 according to the present embodiment are described. Note that the flow charts shown in FIG. 11 to FIG. 13 are only examples of flows of processing by the authentication processing apparatus 1, and the order, etc. of the processing described in each flow chart may be altered as appropriate. For example, pieces of processing related to the application and the imaging of some irradiation lights may be performed collectively in an earlier stage; after that, in regard to all the captured image data, pieces of processing related to the extraction and the authentication of a fingerprint pattern and a vein pattern may be performed collectively in a later stage. Further, one kind of processing may be performed repeatedly.

Further, although in the flow chart shown in FIG. 11 both fingerprint authentication processing and vein authentication processing are performed by the authentication processing apparatus 1, the authentication processing apparatus 1 may perform only one of the pieces of processing.

1.5. Supplements

Correction Processing Utilizing Differences Between Plurality of Captured Images Note that the authentication processing apparatus 1 according to the present embodiment may perform correction based on differences between a plurality of captured images. There is also a case where a captured image generated by the imaging apparatus 10 includes not only a pattern related to a target living body structure or a target living body component, such as a fingerprint or veins, but also a pattern related to other living body structures or living body components. Thus, the image processing unit 231 performs correction using differences between a plurality of captured images that are captured and generated when different irradiation lights are applied. Thus, an unnecessary pattern appearing in a captured image can be removed by the differences.

For example, when scattered light resulting from the second irradiation light passes through a surface of a finger, there is a case where the scattered light is further scattered at ridges of a fingerprint, etc. Hence, there is a possibility that not only a vein pattern but also a fingerprint pattern will be included in a captured image obtained by imaging the scattered light. Thus, as described above, by taking a difference between a captured image (the first captured image) that is captured and generated when the first irradiation light is applied and in which only a fingerprint pattern is included and a captured image (the second captured image) that is captured and generated when the second irradiation light is applied, the fingerprint pattern included in the second captured image can be removed. Thereby, the authentication accuracy of the vein pattern can be improved.

An example of processing related to the removal of a fingerprint pattern included in the second captured image will now be described with reference to FIG. 14A, FIG. 14B, and FIG. 14C.

First, by the control of the imaging control unit 210, the authentication processing apparatus 1 radiates a first irradiation light from the first light source 111, applies the first irradiation light to the interior of the first light guide plate 101, and images injected scattered light (the first captured image). Similarly, by the control of the imaging control unit 210, the authentication processing apparatus 1 radiates a second irradiation light from the second light source 112, applies the second irradiation light to the interior of the second light guide plate 102, and images injected scattered light (the second captured image). Then, the authentication processing apparatus 1 uses the data acquisition unit 220 to acquire captured image data including the generated first captured image and second captured image.

Next, the authentication processing apparatus 1 uses the image processing unit 231 to extract a fingerprint pattern and a vein pattern from the acquired respective captured image data. Here, when extracting a vein pattern from the second captured image, there is a case where a fingerprint pattern is extracted together with the vein pattern.

Figure 14A:
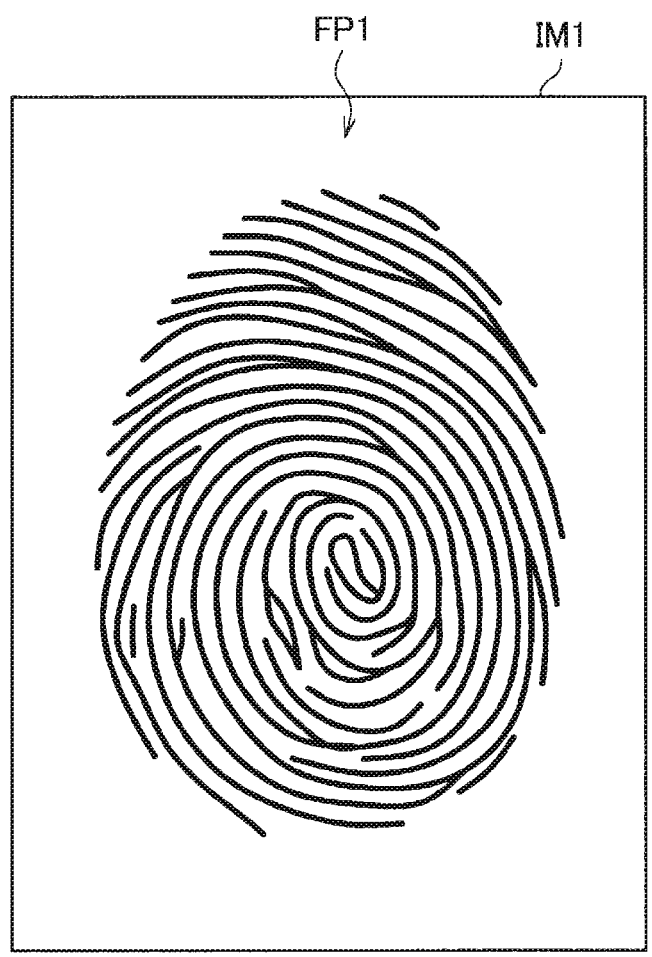
FIG. 14A is a diagram showing an example of a first captured image.
Figure 14B:
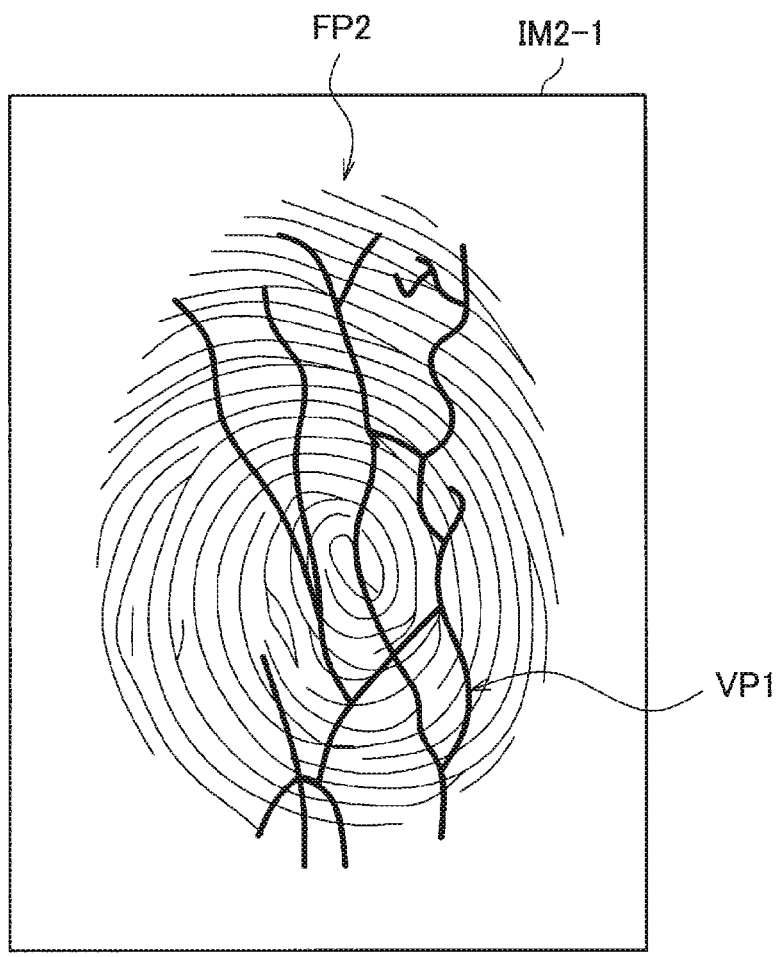
FIG. 14B is a diagram showing an example of a second captured image.

FIG. 14A and FIG. 14B are diagrams showing examples of a first captured image IM1 and a second captured image IM2-1. As shown in FIG. 14A, the first captured image IM1 includes a fingerprint pattern FP1. Further, as shown in FIG. 14B, the second captured image IM2-1 includes a vein pattern VP1 and a fingerprint pattern FP2. The fingerprint pattern FP2 is a pattern that may appear due to the fact that, when scattered light from the interior of the finger passes through the surface of the finger, the scattered light is scattered at ridges of the fingerprint, etc. Hence, although the fingerprint pattern FP1 and the fingerprint pattern FP2 have different luminances etc. on the images, they show substantially the same shape.

Here, by taking a difference between the first captured image IM1 and the second captured image IM2, the image processing unit 231 removes the fingerprint pattern FP2 included in the second captured image IM2-1. Specifically, since the shapes of the fingerprint pattern FP1 and the fingerprint pattern FP2 substantially agree, the fingerprint pattern FP2 included in the second captured image IM2-1 is removed using information related to the fingerprint pattern FP1. Note that known interpolation technology may be applied to the removal of the fingerprint pattern FP2, for example.

Figure 14C:
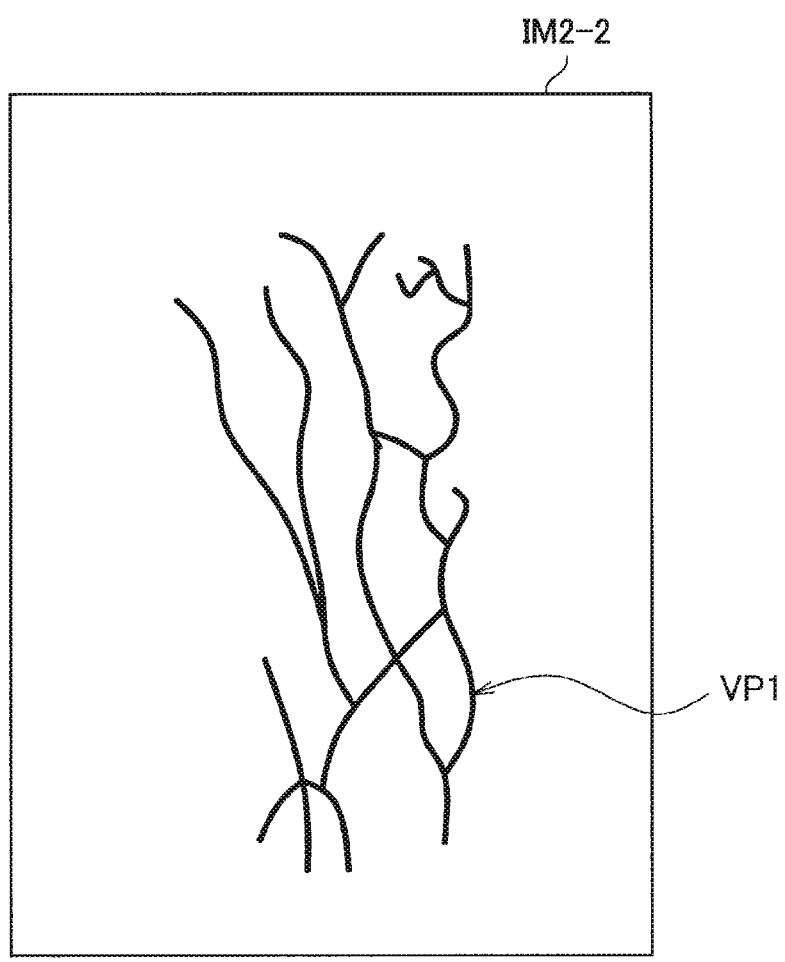
FIG. 14C is a diagram showing an example of the second captured image after removal of a fingerprint pattern.

FIG. 14C is a diagram showing an example of a second captured image IM2-2 after the removal of the fingerprint pattern FP2. As shown in FIG. 14C, by correction processing using the difference between the first captured image IM1 and the second captured image IM2-2 by the image processing unit 231, the fingerprint pattern FP2 is removed from the second captured image IM2-2, and exclusively the vein pattern VP1 can be obtained. Thereby, the accuracy of vein authentication processing can be enhanced in the authentication processing unit 232 in a later stage.

Further, the image processing unit 231 may correct each captured image by using differences between a plurality of captured images to remove noise that may occur due to a substance that tends to absorb near-infrared light or visible light, such as a mole or a freckle, which may exist on a surface of a part of a living body such as a finger, for example. Thereby, for example, various patterns such as a fingerprint pattern and a vein pattern in which the substance is superimposed can be corrected. Note that, in a case where an image corresponding to the substance is removed, there is a possibility that a portion corresponding to the image will be lost from various patterns. In this case, each captured image may be corrected using, for example, a known interpolation algorithm or the like, as appropriate.

1.6. Sub-Conclusion

Hereinabove, the authentication processing apparatus 1 according to the first embodiment of the present disclosure is described. First, the imaging apparatus 10 included in the authentication processing apparatus 1 according to the present embodiment includes a first light guide plate having a mounting region where a part of a living body can be mounted and at least one second light guide plate provided on a surface other than the mounting region; a light source that applies irradiation light to each light guide plate is provided on an edge portion of the light guide plate; and an imaging unit having an imaging function is provided on the opposite side of the first light guide plate from the side where the second light guide plate is provided. By this configuration, the size of the imaging apparatus 10 can be made as small as possible. Therefore, the convenience of the imaging apparatus 10 is improved, and a plurality of pieces of biometric authentication can be performed using only the imaging apparatus 10.

Further, the imaging apparatus 10 includes an optical system including a microlens array, and thereby the imaging apparatus 10 can be further downsized.

Further, by the information processing apparatus 20 included in the authentication processing apparatus 1 according to the present embodiment, patterns related to a plurality of pieces of biometric authentication can be authenticated using a plurality of captured images generated by the imaging apparatus 10. Thereby, complex biometric authentication such as multimodal authentication is enabled. Therefore, the accuracy of biometric authentication processing using the imaging apparatus 10 according to an embodiment of the present disclosure can be improved.

2. Second Embodiment (Configuration Including Analysis Processing)

Next, an authentication processing apparatus 1 according to a second embodiment of the present disclosure is described. The authentication processing apparatus 1 according to the present embodiment has not only the function of performing biometric authentication processing but also the function of performing analysis processing regarding a living body. The analysis function includes, for example, a function related to analysis regarding the skin of a living body, or the analysis of the pulsation of a living body.

Here, the analysis regarding the skin includes, for example, an analysis related to whether an object mounted on the mounting region 1001a of the imaging apparatus 10 is a surface (that is, the skin) of a living body or not, or an evaluation of the nature of the skin (for example, an index called the clearness of the skin). Further, the analysis of the pulsation of a living body may be performed by grasping the transport state of blood in arteries of the living body, as a pulse wave. By performing such analysis processing and causing an analysis result to be used for biometric authentication, more secure biometric authentication can be performed, and an analysis result can be easily associated with a user authenticated by biometric authentication processing.

2.1. Configuration Example

The configuration of the authentication processing apparatus 1 according to the present embodiment is the same as the authentication processing apparatus 1 according to the first embodiment of the present disclosure except for a processing unit 230-2 of the information processing apparatus 20. Hence, in the following, the configuration of the processing unit 230-2 according to the present embodiment is described.

Figure 15:
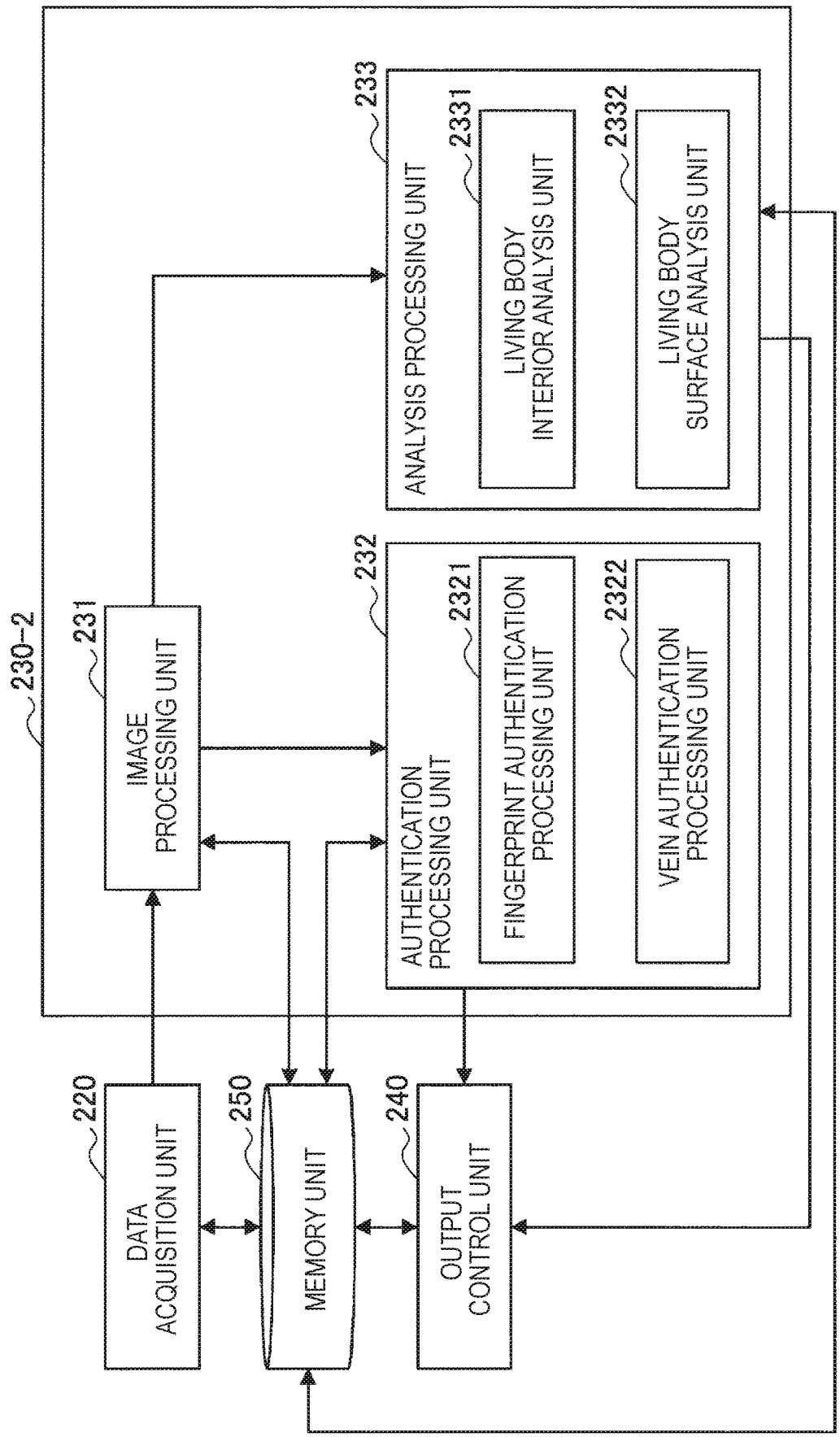
FIG. 15 is a block diagram showing a configuration example of a processing unit according to a second embodiment of the present disclosure.

FIG. 15 is a block diagram showing a configuration example of the processing unit 230-2 according to the present embodiment. As shown in FIG. 15, the processing unit 230-2 according to the present embodiment includes the image processing unit 231, the authentication processing unit 232, and an analysis processing unit 233. Furthermore, the analysis processing unit 233 mainly includes a living body interior analysis unit 2331 and a living body surface analysis unit 2332.

Note that the configuration and function of the image processing unit 231 and the authentication processing unit 232 are the same as those of the image processing unit 231 and the authentication processing unit 232 according to the first embodiment of the present disclosure, and therefore a description is omitted.

Analysis Processing Unit

The analysis processing unit 233 uses image data outputted from the image processing unit 231 to perform analysis processing in regard to the state of a living body. The state of a living body herein includes, as described above, the structure or state of the interior of the living body (for example, pulsation or the thickness of subcutaneous fat) and the structure or state of a surface of the living body (for example, the state of the skin). The analysis processing unit 233 analyzes these states of the living body, and outputs the analysis results to the output control unit 240, the memory unit 250, etc.

The analysis processing unit 233 according to the present embodiment includes the living body interior analysis unit 2331 that analyzes the structure or state of the interior of a living body and the living body surface analysis unit 2332 that analyzes the structure or state of a surface of a living body.

Living Body Interior Analysis Unit

The living body interior analysis unit 2331 uses image data outputted from the image processing unit 231 to analyze the structure or state of the interior of a living body. The image data used here are preferably image data related to the interior of the living body. That is, the imaging apparatus 10 preferably uses a captured image that is captured and generated when the second irradiation light is radiated from the second light source 112 so as to be applied to the interior of a part (for example, a finger) of the living body.

The living body interior analysis unit 2331 may analyze the pulsation of the living body, for example. The pulsation of the living body is obtained by analyzing a pulse wave that reflects the transport state of blood flowing through arteries of the living body. The pulse wave can be obtained by, for example, applying green light or red light to the interior of a part of the living body. The green light or red light scattered in the interior of the living body tends to be absorbed in oxygenated hemoglobin existing in the interiors of arteries. The amount of absorbed scattered light changes in accordance with the amount of transported liquid in the arteries. Therefore, temporal changes in the amount of absorbed scattered light can be grasped as a pulse wave.

To acquire temporal changes in the amount of absorbed scattered light, it is required to consecutively generate captured images while continuously applying irradiation light to the part of the living body. Hence, the data acquisition unit 220 acquires a plurality of captured images consecutively captured and generated, and the living body interior analysis unit 2331 analyzes data that have undergone image processing by the image processing unit 231. For example, the image processing unit 231 extracts the luminance of each of the consecutive captured images, and the living body interior analysis unit 2331 analyzes the pulsation of the living body on the basis of the time-series changes of the luminances of the captured images. By this series of processing, information related to the pulsation of the living body can be obtained. Note that the luminance extracted from the captured image may be a representative value such as the average value, an intermediate value, or the maximum value, which is based on the distribution of the luminances of the pixels of the captured image, or the like.

By obtaining such information related to the pulsation of a living body, for example, even if a pattern related to an imaging object that comes into contact with the mounting region 1001a of the imaging apparatus 10 is authenticated, it can be identified that the imaging object is not a living body (for example, a model simulating a fingerprint pattern or a vein pattern).

Further, the acquired information related to the pulsation of the living body may be associated with personal information authenticated by the authentication processing unit 232. Thereby, history information of the pulsation can be recorded while being associated with the personal information automatically.

Note that the living body interior analysis unit 2331 may also analyze the thickness of subcutaneous fat of a living body, for example. The thickness of subcutaneous fat can be estimated by, for example, applying near-infrared light to a part of a living body to obtain scattered light, imaging the scattered light to generate a captured image, and analyzing the luminance of the captured image.

Living Body Surface Analysis Unit

The living body surface analysis unit 2332 uses image data outputted from the image processing unit 231 to analyze the structure or state of a surface of a living body. The image data used here are preferably image data related to the surface of the living body. That is, the imaging apparatus 10 preferably uses a captured image that is captured and generated when the first irradiation light is radiated from the first light source 111 so that irradiation light is scattered at the contact interface between a surface of a part (for example, a finger) of the living body and the first light guide plate 101.

The living body surface analysis unit 2332 may analyze, for example, whether the imaging object is the skin of a living body or not, or the nature of a skin that is the imaging object. For example, Ohno et al.: "*Maruchibando-Gazo Ni Yoru Bunko-Tokusei-Suitei To Sono Oyo* (Estimation of spectral characteristics based on multiband images and application of the same)," The transactions of the Institute of Electrical Engineers of Japan C, 125, 5, 2005 shows that, in regard to the spectral reflectance characteristics of the skin of a human being, almost fixed reflectance characteristics are exhibited for light of wavelengths of 530 nm to 580 nm and on the other hand reflectance characteristics rapidly increasing with transition to the high wavelength side are exhibited for light of wavelengths of 580 nm to 630 nm, unlike in the colors of the skins of other living bodies.

By utilizing this, whether the imaging object corresponding to a captured image is the skin of a human being or not can be identified by radiating irradiation light from at least one light source that has at least three kinds of different wavelengths, generating captured images corresponding to the irradiation lights, and using the captured images. The at least three kinds of different wavelengths may be, for example, approximately 530 nm, approximately 580 nm, and approximately 630 nm. In this case, for example, the first light sources 111*a* to 111*c* shown in FIG. 2 may be capable of radiating irradiation lights having the wavelengths described above, respectively.

The living body surface analysis unit 2332 analyzes the luminances of the captured images obtained for the irradiation lights having different wavelengths, and can thereby identify whether the imaging object is the skin of a human being or not. For example, an imaging object can be identified as the skin of a human being in a case where the luminances of captured images obtained when irradiation lights having wavelengths of approximately 530 nm and approximately 580 nm are applied are almost at the same level and on the other hand the luminance of a captured image obtained when an irradiation light having a wavelength of approximately 630 nm is applied is a luminance that has increased steeply from the luminances of the other captured images.

By obtaining such information related to the skin of a human being, even if a pattern related to an imaging object that comes into contact with the mounting region 1001*a* of the imaging apparatus 10 is authenticated, it can be identified that the imaging object is not a living body (for example, a model simulating a fingerprint pattern or a vein pattern).

Further, the acquired information related to the skin may be associated with authenticated personal information. Thereby, history information related to the skin can be recorded while being associated with the personal information automatically. Further, also the skin itself can be utilized for biometric authentication, as a skin pattern.

Furthermore, an evaluation regarding the clearness of the skin may be performed on the basis of a result of analysis by the living body surface analysis unit 2332 on the luminance of a captured image corresponding to each irradiation light. In general, it is said that what is called "a clear skin" is a skin having a relatively high reflectance of light at the surface of the skin. Hence, for example, an evaluation regarding the clearness of the skin may be performed on the basis of the magnitude of the luminance of a captured image obtained when an irradiation light having a wavelength of approximately 630 nm is applied.

Further, the living body surface analysis unit 2332 may analyze the amount of melanin pigment contained in the surface of the skin by using a difference between captured images based on scattered lights of near-infrared light and red light. In general, melanin has the characteristic of absorbing more near-infrared light than red light. Hence, the difference between the luminances of captured images based on scattered lights of near-infrared light and infrared light having the same intensity may be in proportion to the amount of melanin pigment. That is, the amount of melanin pigment can be analyzed on the basis of a difference between captured images based on scattered lights of near-infrared light and infrared light.

Note that imaging conditions in the imaging apparatus 10 may be adjusted using the amount of melanin pigment analyzed. For example, the intensity of irradiation light radiated from each light source (in particular, a light source that radiates infrared light or near-infrared light) may be adjusted using the amount of melanin pigment analyzed. More specifically, the intensity of irradiation light may be adjusted to a larger value in accordance with the increase in the amount of melanin pigment. Thereby, a situation where the luminance of a captured image is reduced by the absorption of scattered light by melanin and an unclear pattern is obtained can be prevented. Note that the imaging control unit 210 may perform the adjustment of the intensity of irradiation light on the basis of an analysis result acquired from the processing unit 230-2, for example. Further, for example, the exposure time, aperture, etc. of the imaging unit 120 may be adjusted instead of the intensity of irradiation light.

Hereinabove, the analysis processing unit 233 according to the present embodiment is described. Thus, by combining a result of analysis by the analysis processing unit 233 with an authentication result of the authentication processing unit 232, a masquerade of a part of a living body by a model can be seen through, and unjust authentication can be prevented. Further, the convenience of operation related to the recording of an analysis result by the user can be improved by associating the analysis result with an authentication result.

2.2. Flows of Processing

Figure 16:
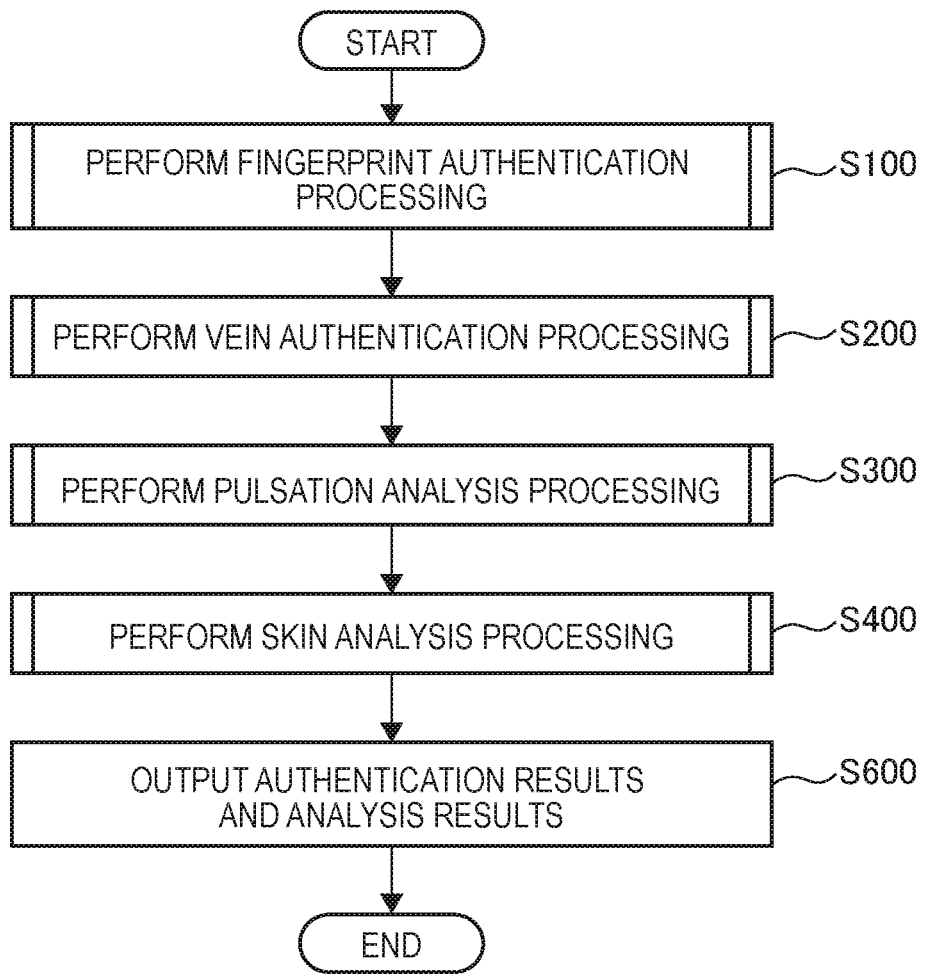
FIG. 16 is a flow chart showing an example of a flow of processing by an authentication processing apparatus according to the embodiment.

Next, examples of flows of processing by the authentication processing apparatus 1 according to the present embodiment are described. FIG. 16 is a flow chart showing an example of a flow of processing by the authentication processing apparatus 1 according to the present embodiment. As shown in the flow chart shown in FIG. 16, the authentication processing apparatus 1 performs fingerprint authentication processing (step S100) and vein authentication processing (step S200), for example. Further, the authentication processing apparatus 1 according to the present embodiment performs pulsation analysis processing (step S300) and skin analysis processing (step S400), for example. Note that the order of these pieces of processing is not limited to the order according to the flow chart shown in FIG. 16. Further, the flows of processing in fingerprint authentication processing and vein authentication processing are the same as the respective pieces of processing according to the first embodiment of the present disclosure;

hence, in the following, examples of flows of processing in pulsation analysis processing and skin analysis processing by the authentication processing apparatus 1 according to the present embodiment are described.

Pulsation Analysis Processing

Figure 17:
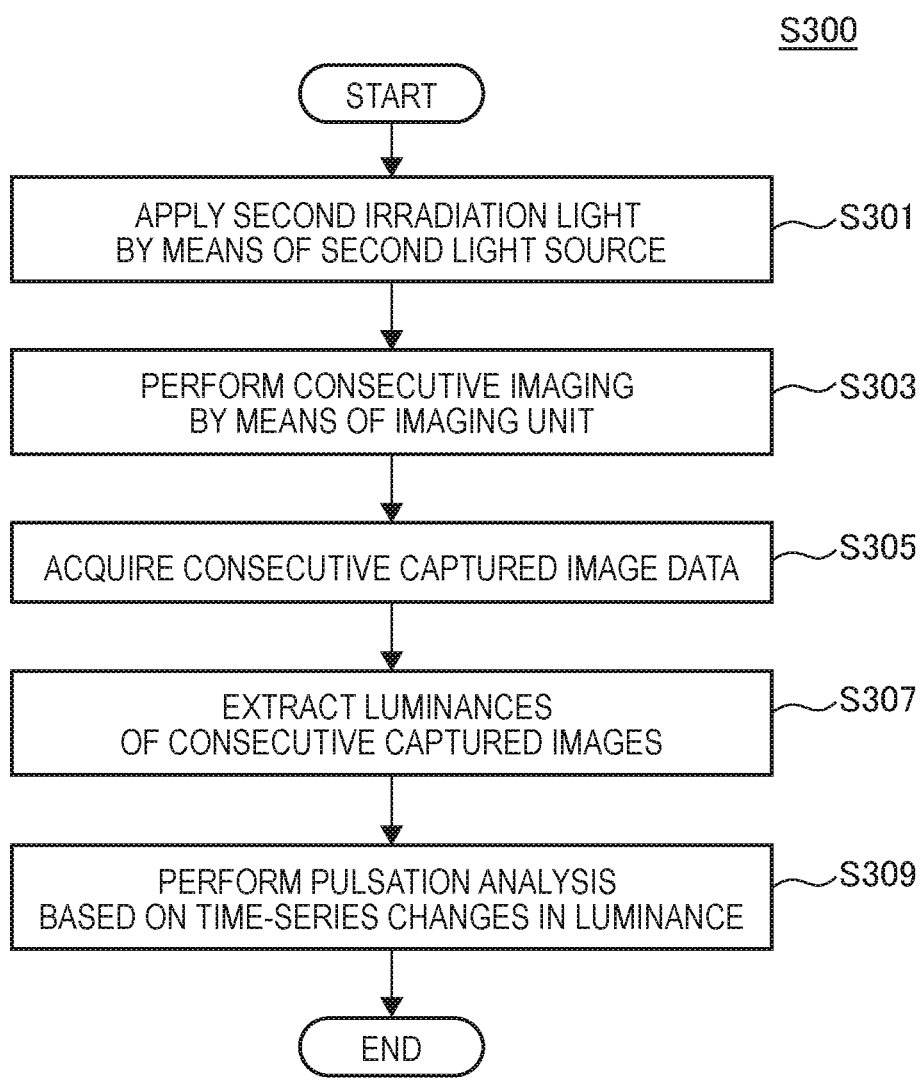
FIG. 17 is a flow chart showing an example of a flow of pulsation analysis processing by the authentication processing apparatus according to the embodiment.

FIG. 17 is a flow chart showing an example of a flow of pulsation analysis processing by the authentication processing apparatus 1 according to the present embodiment. Referring to FIG. 17, first, by the control of the imaging control unit 210, the authentication processing apparatus 1 radiates a second irradiation light from the second light source 112, and applies the second irradiation light to the interior of the second light guide plate 102 (step S301). Further, the authentication processing apparatus 1 uses the imaging unit 120 to consecutively image the injected scattered light (step S303).

Note that, in step S301, while the imaging of scattered light by the imaging unit 120 continues, the second irradiation light is radiated continuously or intermittently from the second light source 112. In a case where the second irradiation light is being radiated intermittently, the radiation timing of the second irradiation light is synchronized with the timing of imaging by the imaging unit 120. Further, the captured image generated by the imaging unit 120 may be a moving image. Note that the second irradiation light preferably has a wavelength corresponding to green light or red light.

Next, the authentication processing apparatus 1 uses the data acquisition unit 220 to acquire the generated consecutive captured image data (step S305).

Next, the authentication processing apparatus 1 uses the processing unit 230-2 (the image processing unit 231) to extract the luminance of each of the acquired consecutive captured images (step S307). Then, the authentication processing apparatus 1 uses the processing unit 230-2 (the living body interior analysis unit 2331 of the analysis processing unit 233) to analyze the pulsation on the basis of the time-series changes in luminance (S309).

The pulsation analysis processing mentioned above may be performed continuously for a prescribed period of time. The prescribed period of time may be, for example, a time in which the part of the living body is mounted on the mounting region 1001a of the first light guide plate 101, and is determined by the imaging control unit 210, as appropriate.

Skin Analysis Processing

FIG. 18 is a flow chart showing an example of a flow of skin analysis processing by the authentication processing apparatus 1 according to the present embodiment. Referring to FIG. 18, first, by the control of the imaging control unit 210, the authentication processing apparatus 1 radiates a first wavelength light having a first wavelength from the first light source 111, and applies the first wavelength light to the interior of the first light guide plate 101 (step S401). Further, the authentication processing apparatus 1 uses the imaging unit 120 to image the injected scattered light (step S403).

Similarly, the authentication processing apparatus 1 applies a second wavelength light having a second wavelength to the interior of the first light guide plate 101 from the first light source 111 (step S405), and images the injected scattered light (step S407). Further, the authentication processing apparatus 1 applies a third wavelength light having a third wavelength to the interior of the first light guide plate 101 from the first light source 111 (step S409), and images the injected scattered light (step S411).

Next, the authentication processing apparatus 1 uses the data acquisition unit 220 to acquire each of the generated captured image data (step S413).

Next, the authentication processing apparatus 1 uses the processing unit 230-2 (the image processing unit 231) to extract the luminance of each of the acquired captured images (step S415). Then, the authentication processing apparatus 1 uses the processing unit 230-2 (the living body surface analysis unit 2332 of the analysis processing unit 233) to perform analysis regarding the skin of the living body on the basis of the relationship between the wavelength and the luminance of each wavelength light (S417).

Referring to FIG. 16 again, the authentication processing apparatus 1 uses the output control unit 240 to output the authentication results in fingerprint authentication processing and vein authentication processing and the analysis results in pulsation analysis processing and skin analysis processing (step S600).

Hereinabove, examples of flows of processing by the authentication processing apparatus 1 according to the present embodiment are described. Note that the flow charts shown in FIG. 16 to FIG. 18 are only examples of flows of processing by the authentication processing apparatus 1, and the order, etc. of the processing described in each flow chart may be altered as appropriate.

Further, although in the flow chart shown in FIG. 16 both pulsation analysis processing and skin analysis processing are performed by the authentication processing apparatus 1, the authentication processing apparatus 1 may perform only one of the pieces of processing. Further, although in the skin analysis processing mentioned above a plurality of wavelength lights are radiated from the first light source 111, a plurality of wavelength lights may be radiated from the second light source 112.

2.3. Sub-Conclusion

Hereinabove, the authentication processing apparatus 1 according to the first embodiment of the present disclosure is described. By this configuration, analysis processing regarding a living body can be combined with processing related to biometric authentication. Thereby, not only can a pattern such as a fingerprint pattern or a vein pattern be recognized, but also whether an imaging object corresponding to the pattern is a living body or not can be identified. That is, a masquerade of a living body having a pattern corresponding to a template can be prevented.

Further, a result of analysis processing regarding a living body can be recorded while being associated with personal information of a user who has undergone biometric authentication. That is, biometric authentication and analysis regarding a living body can be performed simultaneously. Therefore, for example, convenience is improved for a user who wants to perform analysis regarding the skin or health, and an analysis result can be recorded in a memory unit, a cloud, etc. securely.

3. Hardware Configuration Example

Next, with reference to FIG. 19, a hardware configuration of an information processing apparatus according to an embodiment of the present disclosure is described. FIG. 19 is a block diagram showing a hardware configuration example of the information processing apparatus according to the embodiment of the present disclosure. An illustrated information processing apparatus 900 can realize the information processing apparatus 20 in the above described embodiment.

The information processing apparatus 900 includes a CPU 901, read only memory (ROM) 903, and random access memory (RAM) 905. In addition, the information processing apparatus 900 may include a host bus 907, a bridge 909, an external bus 911, an interface 913, an input device 915, an output device 917, a storage device 919, a drive 921, a connection port 925, and a communication device 929. The information processing apparatus 900 may include a processing circuit such as a digital signal processor (DSP) or an application-specific integrated circuit (ASIC), instead of or in addition to the CPU 901.

The CPU 901 functions as an arithmetic processing device and a control device, and controls the overall operation or a part of the operation of the information processing apparatus 900 according to various programs recorded in the ROM 903, the RAM 905, the storage device 919, or a removable storage medium 923. For example, the CPU 901 controls overall operations of respective function units included in the information processing apparatus 20 of the above-described embodiment. The ROM 903 stores programs, operation parameters, and the like used by the CPU 901. The RAM 905 transiently stores programs used when the CPU 901 is executed, and parameters that change as appropriate when executing such programs. The CPU 901, the ROM 903, and the RAM 905 are connected with each other via the host bus 907 configured from an internal bus such as a CPU bus or the like. The host bus 907 is connected to the external bus 911 such as a Peripheral Component Interconnect/Interface (PCI) bus via the bridge 909.

The input device 915 is a device operated by a user such as a mouse, a keyboard, a touchscreen, a button, a switch, and a lever. The input device 915 may be a remote control device that uses, for example, infrared radiation and another type of radio waves. Alternatively, the input device 915 may be an external connection device 927 such as a mobile phone that corresponds to an operation of the information processing apparatus 900. The input device 915 includes an input control circuit that generates input signals on the basis of information which is input by a user to output the generated input signals to the CPU 901. The user inputs various types of data and indicates a processing operation to the information processing apparatus 900 by operating the input device 915.

The output device 917 includes a device that can visually or audibly report acquired information to a user. The output device 917 may be, for example, a display device such as an LCD, a PDP, and an OELD, an audio output device such as a speaker and a headphone, and a printer. The output device 917 outputs a result obtained through a process performed by the information processing apparatus 900, in the form of text or video such as an image, or sounds such as audio sounds.

The storage device 919 is a device for data storage that is an example of a storage unit of the information processing apparatus 900. The storage device 919 includes, for example, a magnetic storage device such as a hard disk drive (HDD), a semiconductor storage device, an optical storage device, or a magneto-optical storage device. The storage device 919 stores therein the programs and various data executed by the CPU 901, and various data acquired from an outside. Further, the storage device 919 can realize the function of the memory unit 250 according to the above embodiments.

The drive 921 is a reader/writer for the removable storage medium 923 such as a magnetic disk, an optical disc, a magneto-optical disk, and a semiconductor memory, and built in or externally attached to the information processing apparatus 900. The drive 921 reads out information recorded on the mounted removable storage medium 923, and outputs the information to the RAM 905. The drive 921 writes the record into the mounted removable storage medium 923.

The connection port 925 is a port used to directly connect devices to the information processing apparatus 900. The connection port 925 may be a Universal Serial Bus (USB) port, an IEEE1394 port, or a Small Computer System Interface (SCSI) port, for example. The connection port 925 may also be an RS-232C port, an optical audio terminal, a High-Definition Multimedia Interface (HDMI (registered trademark)) port, and so on. The connection of the external connection device 927 to the connection port 925 makes it possible to exchange various kinds of data between the information processing apparatus 900 and the external connection device 927.

The communication device 929 is a communication interface including, for example, a communication device for connection to a communication network NW. The communication device 929 may be, for example, a wired or wireless local area network (LAN), Bluetooth (registered trademark), or a communication card for a wireless USB (WUSB). The communication device 929 may also be, for example, a router for optical communication, a router for asymmetric digital subscriber line (ADSL), or a modem for various types of communication. For example, the communication device 929 transmits and receives signals in the Internet or transits signals to and receives signals from another communication device by using a predetermined protocol such as TCP/IP. The communication network NW to which the communication device 929 connects is a network established through wired or wireless connection. The communication network NW is, for example, the Internet, a home LAN, infrared communication, radio wave communication, or satellite communication.

The example of the hardware configuration of the information processing apparatus 900 has been introduced.

4. Conclusion

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

For example, although in the above embodiments the authentication processing apparatus 1 includes the imaging apparatus 10 and the information processing apparatus 20, the present technology is not limited to this example. For example, in a case where a control device of a CPU, a ROM, a RAM, etc. and a memory device such as a storage are further provided in the imaging apparatus 10, the imaging apparatus 10 may include the functions held by the information processing apparatus 20. In this case, the authentication processing apparatus 1 is obtained using the imaging apparatus 10. Further, the information processing apparatus 20 may include the functions held by the imaging apparatus 10. In this case, the authentication processing apparatus 1 is obtained using the information processing apparatus 20. Further, the imaging apparatus 10 may have part of the functions held by the information processing apparatus 20, and the information processing apparatus 20 may have part of the functions held by the imaging apparatus 10.

Further, although the imaging apparatus 10 according to the above embodiments is used in order to acquire a fingerprint pattern and a vein pattern of a finger, the present technology is not limited to this example. For example, the imaging apparatus 10 according to the present technology may be used for the analysis of the blood concentration and blood components of blood. In this case, the blood concentration and blood components can be analyzed by utilizing distributions of luminances and changes in luminance of captured images captured by the imaging apparatus 10, for example.

The steps in the processes performed by the information processing apparatus in the present specification may not necessarily be processed chronologically in the orders described in the flowcharts. For example, the steps in the processes performed by the information processing apparatus may be processed in different orders from the orders described in the flowcharts or may be processed in parallel.

Also, a computer program causing hardware such as the CPU, the ROM, and the RAM included in the information processing apparatus to carry out the equivalent functions as the above-described configuration of the information processing apparatus can be generated. Also, a storage medium having the computer program stored therein can be provided.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)
An imaging apparatus including:
a first light guide plate having a mounting surface including a mounting region where a part of a living body is to be mounted;
a second light guide plate provided on the mounting surface excluding the mounting region;
at least one first light source provided on an edge portion of the first light guide plate and configured to radiate first irradiation light of a prescribed wavelength to an interior of the first light guide plate;
at least one second light source provided on an edge portion of the second light guide plate and configured to radiate second irradiation light of a prescribed wavelength to an interior of the second light guide plate; and
an imaging unit placed on a side of a surface of the first light guide plate on an opposite side to the second light guide plate and configured to image light coming from a surface of the part of the living body.

(2)
The imaging apparatus according to (1),
in which the wavelength of the first irradiation light is different from the wavelength of the second irradiation light.

(3)
The imaging apparatus according to (2),
in which the first light guide plate contains an optical material in which the wavelength of the first irradiation light and the wavelength of the second irradiation light are included in a passband, and
the second light guide plate contains an optical material in which the wavelength of the first irradiation light is included in a stopband.

(4)
The imaging apparatus according to any one of (1) to (3),
in which a plurality of the first light sources are provided on the edge portion of the first light guide plate, and
respective wavelengths of the first irradiation lights applied from the first light sources are different from each other.

(5)
The imaging apparatus according to any one of (1) to (4),
in which a timing of radiation of the first irradiation light by the first light source is different from a timing of radiation of the second irradiation light by the second light source.

(6)
The imaging apparatus according to any one of (1) to (5),
in which the imaging unit includes an imaging element provided with an optical system including a microlens array in which a plurality of microlenses are arranged in a lattice configuration.

(7)
The imaging apparatus according to (6),
in which a thickness of the first light guide plate is more than or equal to a separation distance between the microlens array and the first light guide plate.

(8)
The imaging apparatus according to any one of (1) to (7),
in which a light blocking body is further provided between the first light guide plate and the second light guide plate.

(9)
The imaging apparatus according to any one of (1) to (8),
in which a third light guide plate is further provided on a side of a surface of the second light guide plate on an opposite side to the first light guide plate, and
at least one third light source configured to apply third irradiation light to an interior of the third light guide plate is further provided on an edge portion of the third light guide plate.

(10)
An authentication processing apparatus including:
an imaging apparatus including
a first light guide plate having a mounting surface including a mounting region where a part of a living body is to be mounted,
a second light guide plate provided on the mounting surface excluding the mounting region,
at least one first light source provided on an edge portion of the first light guide plate and configured to apply first irradiation light of a prescribed wavelength to an interior of the first light guide plate,
at least one second light source provided on an edge portion of the second light guide plate and configured to apply second irradiation light of a prescribed wavelength to an interior of the second light guide plate, and
an imaging unit placed on a side of a surface of the first light guide plate on an opposite side to the second light guide plate and configured to image light coming from a surface of the part of the living body and generate a captured image; and
an information processing apparatus including
a processing unit configured to perform processing regarding the living body including at least biometric authentication on a basis of the captured image generated in a state where the part of the living body is mounted on the mounting region.

(11) The authentication processing apparatus according to (10),
in which the processing unit performs processing regarding authentication of the living body on a basis of a first captured image generated by the imaging unit when the first irradiation light is applied and a second captured image generated by the imaging unit when the second irradiation light is applied.

(12) The authentication processing apparatus according to (11),
in which the processing unit performs fingerprint authentication processing of the living body on a basis of the first captured image, and performs vein authentication processing of the living body on a basis of the second captured image.

(13) The authentication processing apparatus according to (11) or (12),
in which the processing unit performs correction of the second captured image generated by the imaging unit, on a basis of a difference between the first captured image and the second captured image.

(14) The authentication processing apparatus according to (13),
in which the processing unit performs correction of a vein pattern included in the second captured image by using a fingerprint pattern of the living body included in the first captured image.

(15) The authentication processing apparatus according to any one of (11) to (14), further including:
an imaging control unit configured to adjust an imaging condition of the imaging apparatus on a basis of a difference between the first captured image and the second captured image.

(16) The authentication processing apparatus according to any one of (10) to (15),
in which the processing unit further performs processing regarding a temporal change of a state of the living body on a basis of a time-series change of captured images consecutively generated by the imaging unit.

(17) The authentication processing apparatus according to any one of (10) to (16),
in which the wavelengths of the first irradiation light and the second irradiation light are selected in accordance with the processing regarding the living body.

(18) An imaging method including:
applying first irradiation light of a prescribed wavelength from an edge portion of a first light guide plate having a mounting surface including a mounting region where a part of a living body is to be mounted, to an interior of the first light guide plate, in a state where the part of the living body is caused to be mounted on the mounting region;
applying second irradiation light of a prescribed wavelength from an edge portion of a second light guide plate provided on the mounting surface excluding the mounting region, to an interior of the second light guide plate, in a state where the part of the living body is caused to be mounted on the mounting region; and
imaging light coming from a surface of the part of the living body, from a side of a surface of the first light guide plate on an opposite side to the second light guide plate, while applying at least one of the first irradiation light or the second irradiation light.

(19) An authentication processing method including:
applying first irradiation light of a prescribed wavelength from an edge portion of a first light guide plate having a mounting surface including a mounting region where a part of a living body is to be mounted, to an interior of the first light guide plate, in a state where the part of the living body is caused to be mounted on the mounting region;
applying second irradiation light of a prescribed wavelength from an edge portion of a second light guide plate provided on the mounting surface excluding the mounting region, to an interior of the second light guide plate, in a state where the part of the living body is caused to be mounted on the mounting region;
imaging light coming from a surface of the part of the living body, from a side of a surface of the first light guide plate on an opposite side to the second light guide plate, while applying at least one of the first irradiation light or the second irradiation light, and generating a captured image; and
performing processing regarding the living body including at least biometric authentication on a basis of the generated captured image.

(20) A program for causing a computer to execute a processing function of performing processing regarding a living body including at least biometric authentication on a basis of a captured image generated in a state where a part of the living body is mounted on a mounting region,
the computer being capable of communicating with an imaging apparatus including
a first light guide plate having a mounting surface including the mounting region where the part of the living body is to be mounted,
a second light guide plate provided on the mounting surface excluding the mounting region,
at least one first light source provided on an edge portion of the first light guide plate and configured to apply first irradiation light of a prescribed wavelength to an interior of the first light guide plate,
at least one second light source provided on an edge portion of the second light guide plate and configured to apply second irradiation light of a prescribed wavelength to an interior of the second light guide plate, and
an imaging unit placed on a side of a surface of the first light guide plate on an opposite side to the second light guide plate and configured to image light coming from a surface of the part of the living body and generate the captured image.

REFERENCE SIGNS LIST 1 authentication processing apparatus
10 imaging apparatus
20 information processing apparatus
101 first light guide plate
102 second light guide plate
103 third light guide plate 111 first light source
112 second light source
113 third light source
120 imaging unit
121 microlens array
122 microlens
123 imaging element
124 light blocking body
131 first light blocking body
132 second light blocking body
210 imaging control unit
220 data acquisition unit
230 (230-1, 230-2) processing unit
231 image processing unit
232 authentication processing unit
233 analysis processing unit
240 output control unit
250 memory unit
1001 mounting surface
1001a mounting region
2321 fingerprint authentication processing unit
2322 vein authentication processing unit
2331 living body interior analysis unit
2332 living body surface analysis unit

The invention claimed is:

1. An imaging apparatus, comprising:
a first light guide plate having a mounting surface including a mounting region where a part of a living body is to be mounted;
a second light guide plate provided on the mounting surface excluding the mounting region;
at least one first light source provided on an edge portion of the first light guide plate and configured to radiate first irradiation light of a prescribed wavelength to an interior of the first light guide plate;
at least one second light source provided on an edge portion of the second light guide plate and configured to radiate second irradiation light of a prescribed wavelength to an interior of the second light guide plate; and
an imaging unit placed on a side of a surface of the first light guide plate on an opposite side to the second light guide plate and configured to image light coming from a surface of the part of the living body.

2. The imaging apparatus according to claim 1,
wherein the prescribed wavelength of the first irradiation light is different from the prescribed wavelength of the second irradiation light.

3. The imaging apparatus according to claim 2,
wherein the first light guide plate contains an optical material in which the prescribed wavelength of the first irradiation light and the prescribed wavelength of the second irradiation light are included in a passband, and
the second light guide plate contains an optical material in which the prescribed wavelength of the first irradiation light is included in a stopband.

4. The imaging apparatus according to claim 1,
wherein a plurality of the first light sources are provided on the edge portion of the first light guide plate, and
respective wavelengths of the first irradiation lights applied from the first light sources are different from each other.

5. The imaging apparatus according to claim 1,
wherein a timing of radiation of the first irradiation light by the first light source is different from a timing of radiation of the second irradiation light by the second light source.

6. The imaging apparatus according to claim 1,
wherein the imaging unit includes an imaging element provided with an optical system including a microlens array in which a plurality of microlenses are arranged in a lattice configuration.

7. The imaging apparatus according to claim 6,
wherein a thickness of the first light guide plate is more than or equal to a separation distance between the microlens array and the first light guide plate.

8. The imaging apparatus according to claim 1,
wherein a light blocking body is further provided between the first light guide plate and the second light guide plate.

9. The imaging apparatus according to claim 1,
wherein a third light guide plate is further provided on a side of a surface of the second light guide plate on an opposite side to the first light guide plate, and
at least one third light source configured to apply third irradiation light to an interior of the third light guide plate is further provided on an edge portion of the third light guide plate.

10. An authentication processing apparatus, comprising:
an imaging apparatus including:
a first light guide plate having a mounting surface including a mounting region where a part of a living body is to be mounted,
a second light guide plate provided on the mounting surface excluding the mounting region,
at least one first light source provided on an edge portion of the first light guide plate and configured to apply first irradiation light of a prescribed wavelength to an interior of the first light guide plate,
at least one second light source provided on an edge portion of the second light guide plate and configured to apply second irradiation light of a prescribed wavelength to an interior of the second light guide plate, and
an imaging unit placed on a side of a surface of the first light guide plate on an opposite side to the second light guide plate and configured to image light coming from a surface of the part of the living body and generate a captured image; and
an information processing apparatus including
a processing unit configured to perform processing regarding the living body including at least biometric authentication on a basis of the captured image generated in a state where the part of the living body is mounted on the mounting region.

11. The authentication processing apparatus according to claim 10,
wherein the processing unit performs processing regarding authentication of the living body on a basis of a first captured image generated by the imaging unit when the first irradiation light is applied and a second captured image generated by the imaging unit when the second irradiation light is applied.

12. The authentication processing apparatus according to claim 11,
wherein the processing unit performs fingerprint authentication processing of the living body on a basis of the first captured image, and performs vein authentication processing of the living body on a basis of the second captured image.

13. The authentication processing apparatus according to claim 11,
wherein the processing unit performs correction of the second captured image generated by the imaging unit, on a basis of a difference between the first captured image and the second captured image.

14. The authentication processing apparatus according to claim 13,
wherein the processing unit performs correction of a vein pattern included in the second captured image by using a fingerprint pattern of the living body included in the first captured image.

15. The authentication processing apparatus according to claim 11, further comprising:
an imaging control unit configured to adjust an imaging condition of the imaging apparatus on a basis of a difference between the first captured image and the second captured image.

16. The authentication processing apparatus according to claim 10,
wherein the processing unit further is further configured to perform processing regarding a temporal change of a state of the living body on a basis of a time-series change of captured images consecutively generated by the imaging unit.

17. The authentication processing apparatus according to claim 10,
wherein the prescribed wavelength of the first irradiation light and the prescribed wavelength of the second irradiation light are selected in accordance with the processing regarding the living body.

18. An imaging method, comprising:
applying first irradiation light of a prescribed wavelength from an edge portion of a first light guide plate having a mounting surface including a mounting region where a part of a living body is to be mounted, to an interior of the first light guide plate, in a state where the part of the living body is caused to be mounted on the mounting region;
applying second irradiation light of a prescribed wavelength from an edge portion of a second light guide plate provided on the mounting surface excluding the mounting region, to an interior of the second light guide plate, in a state where the part of the living body is caused to be mounted on the mounting region; and
imaging light coming from a surface of the part of the living body, from a side of a surface of the first light guide plate on an opposite side to the second light guide plate, while applying at least one of the first irradiation light or the second irradiation light.

19. An authentication processing method, comprising:
applying first irradiation light of a prescribed wavelength from an edge portion of a first light guide plate having a mounting surface including a mounting region where a part of a living body is to be mounted, to an interior of the first light guide plate, in a state where the part of the living body is caused to be mounted on the mounting region;
applying second irradiation light of a prescribed wavelength from an edge portion of a second light guide plate provided on the mounting surface excluding the mounting region, to an interior of the second light guide plate, in a state where the part of the living body is caused to be mounted on the mounting region;
imaging light coming from a surface of the part of the living body, from a side of a surface of the first light guide plate on an opposite side to the second light guide plate, while applying at least one of the first irradiation light or the second irradiation light, and generating a captured image; and
performing processing regarding the living body including at least biometric authentication on a basis of the generated captured image.

20. A non-transitory storage device having stored thereon, a computer-executable program for causing a computer to execute a processing function for performing processing operations regarding a living body, the processing operations comprising:
authenticating by biometric authentication on a basis of a captured image generated in a state where a part of the living body is mounted on a mounting region; and
communicating with an imaging apparatus including
a first light guide plate having a mounting surface including the mounting region where the part of the living body is to be mounted,
a second light guide plate provided on the mounting surface excluding the mounting region,
at least one first light source provided on an edge portion of the first light guide plate and configured to apply first irradiation light of a prescribed wavelength to an interior of the first light guide plate,
at least one second light source provided on an edge portion of the second light guide plate and configured to apply second irradiation light of a prescribed wavelength to an interior of the second light guide plate, and
an imaging unit placed on a side of a surface of the first light guide plate on an opposite side to the second light guide plate and configured to image light coming from a surface of the part of the living body and generate the captured image.

* * * * *